US007186413B2

(12) United States Patent
Bouhadir et al.

(10) Patent No.: US 7,186,413 B2
(45) Date of Patent: Mar. 6, 2007

(54) HYDROGELS AND WATER SOLUBLE POLYMERIC CARRIERS FOR DRUG DELIVERY

(75) Inventors: Kamal H. Bouhadir, Ann Arbor, MI (US); Genevieve M. Kruger, Ann Arbor, MI (US); David J. Mooney, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 319 days.

(21) Appl. No.: 10/445,026

(22) Filed: May 27, 2003

(65) Prior Publication Data

US 2004/0028745 A1 Feb. 12, 2004

Related U.S. Application Data

(62) Division of application No. 09/830,955, filed as application No. PCT/US99/23396 on Oct. 8, 1999, now abandoned.

(60) Provisional application No. 60/103,595, filed on Oct. 9, 1998.

(51) Int. Cl.
*A61K 7/00* (2006.01)
(52) U.S. Cl. ................................. 424/400
(58) Field of Classification Search ................ 424/400; 514/2; 549/510, 511
See application file for complete search history.

(56) References Cited

U.S. PATENT DOCUMENTS 4,489,065 A   12/1984 Walton et al.

| | | | |
|---|---|---|---|
| 5,192,661 A | * | 3/1993 | Roy et al. ................ 435/7.23 |
| 5,547,981 A | * | 8/1996 | Greenwald et al. ......... 514/449 |
| 5,648,506 A | * | 7/1997 | Desai et al. ................ 549/510 |

FOREIGN PATENT DOCUMENTS

| | | |
|---|---|---|
| DE | 1 178 837 B1 | 10/1964 |
| DE | 1178837 B | 10/1964 |
| EP | 0251905 | 1/1988 |
| EP | 0 605 963 A2 | 7/1994 |
| EP | 652015 | 5/1995 |
| EP | 947201 | 10/1999 |
| US | EP 0 606 963 * | 7/1994 |
| WO | WO 93/18793 A1 | 9/1993 |
| WO | WO 9407536 | 4/1994 |
| WO | WO 94/28024 A1 | 12/1994 |
| WO | WO 95/15168 A1 | 6/1995 |

(Continued)

OTHER PUBLICATIONS

Heindel N D et al: "Hydrazide Pharmaceuticals as Conjugates to Polyaldehyde Dextran: Syntheses, Characterization, and Stability" Bioconjugate Chemistry, US,American Chemical Society, Washington, vol. 1, No. 1, Jan. 1, 1990, pp. 77-82, XP00236575 ISSN: 1043-1802.

(Continued)

*Primary Examiner*—Johann Richter
*Assistant Examiner*—Konata M. George

(57) ABSTRACT

Carriers for drug delivery, methods of making such carriers and for associating them to drugs, the resulting carrier and drug combination and methods for drug delivery, particularly controlled or sustained release delivery, using such carrier and drug combinations.

13 Claims, 13 Drawing Sheets

FOREIGN PATENT DOCUMENTS

| WO | WO 9530411 | 11/1995 |
| WO | WO 9624377 | 8/1996 |
| WO | WO 98/12228 A1 | 3/1998 |
| WO | WO 9812228 | 3/1998 |

OTHER PUBLICATIONS

Lee, Kuen Yong et al: "Degradation Behavior of Covalently Crosslinked Poly(aldehyde guluronate) Hydrogels" Macromolecules (2000), 33(1), 97-101, XP000901406.

Bouhadir, K. H. (1) et al: "Synthesis and cross-linking of partially oxidized alginate for tissue engineering applications." Abstracts of Papers American Chemical Society, (1998), vol. 216, No. 1-3, pp. BTEC 78, Meeting Info.: 216th National Meeting of the American Chemical Society Boston, Massachusetts, USA Aug. 23-27, 1998 American Chemical Society., XP000901592.

Bouhadir, Kamal H. et al: "Biodegradable hydrogels for controlled cell and drug delivery" Polym. Prepr. (Am. Chem. Soc., Div. Polym. Chem.) (1999), 40(1), 501-502, XP000901532.

* cited by examiner

HYDROGELS AND WATER SOLUBLE POLYMERIC CARRIERS FOR DRUG DELIVERY

This application is a divisional of U.S. application Ser. No. 09/830,955, filed Aug. 21, 2001, now abandoned; application Ser. No. 09/830,955 is a 371 National phase of PCT/US99/23396 filed Oct. 8, 1999. This application claims benefit of U.S. Provisional Application No. 60/103,595, filed Oct. 9, 1998.

The invention includes carriers for drug delivery, methods of making such carriers and for associating them to drugs, the resulting carrier and drug combination and methods for drug delivery, particularly controlled or sustained release delivery, using such carrier and drug combinations.

In one aspect of the invention hydrogels of modified alginates or other polysaccharide gels are provided as carriers with drugs associated to them by biodegradeable covalent bonds, ionic bonds and/or by diffusion control within the gel. A variety of release profiles of the drugs or prodrugs thereof can be obtained with release rates ranging, for example, from a few days to several months, particularly from three weeks to four months. In a preferred embodiment, alginates are treated to reduce their molecular weight so that they are of a size which is biodegradeable and biocompatible, crosslinked covalently and/or ionically through the action of divalent cations and reacted with a drug or prodrug so that they are degradeably bonded to the alginate. The extent of lowering of the molecular weight and of covalent or ionic crosslinking can be adjusted to provide mechanical properties and degradation rates which are suitable for the particular application. Applications include, but are not limited to, delivery of chemotherapy drugs, growth factors for localized vascularization, steroids for contraception or hormone replacement therapy and localized delivery of drugs following angioplasty to prevent smooth muscle cell proliferation.

In another aspect of the invention, preferably water-soluble polymers are modified so that they can reversibly bind multiple molecules of drug per molecule of polymer. These polymer-drug conjugates can be administered as prodrugs to give a sustained release of the active drug over time. Advantages thereof include a decrease in toxicity effects of the free drug, economizing of the amount of drug needed due to an increase in circulation time and facilitating solubilization of hydrophobic drugs. The particular polymer and molecular weight thereof can be selected to suit the particular application, of which chemotherapy applications are of particular interest.

Hydrogels have been extensively investigated as drug delivery carriers in biomedical applications. They are relatively inexpensive and well suited to deliver drugs in a minimally invasive manner. For example, hydrogels have been widely investigated as delivery vehicles for the localized, sustained release of antineoplastic agents (Jeong et al., Biodegradable block copolymers as injectable drug delivery systems. Nature 1997, 388, 860–861; and Patil et al., Macroporous poly(sucrose acrylate) hydrogel for controlled release of macromolecules. Biomaterials 1996, 17, 2343–2350). Many synthetic and naturally derived materials have been reported to form hydrogels (Hubbell, J. A., Hydrogel systems for barriers and local drug delivery in the control of wound healing. J. Control. Rel. 1996, 39, 305–313; Inoue et al., A hydrophobically-modified bioadhesive polyelectrolyte hydrogel for drug delivery. J. Control. Rel. 1997, 49, 167–176; Zhao et al., Novel degradeable poly(ethylene glycol) hydrogels for controlled release of protein. J. Pharm. Sc. 1998, 87, 1450–1458; and Andreopolos et al., Photoscissable hydrogel synthesis via rapid photopolymerization of novel PEG-based polymers in the absence of photoinitiators. J. Am. Chem. Soc. 1996, 118, 6235–6240), and one widely used hydrogel is formed from the ionic cross-linking of sodium alginate, a linear polysaccharide isolated from seaweed. Alginate is comprised of (1,4)-linked β-D-mannuronic and α-L-guluronic acid residues arranged in blocks of polymannuronate, polyguluronate, and alternating units of both sugars. Divalent cations, such as calcium, ionically cross-link the carboxylate groups on adjacent alginate strands to form hydrogels. The polyguluronate block of alginate is known to be responsible for this gelling feature (Sutherland, I. W. Alginates. In Biomaterials: novel materials from biological sources, Byron D., Ed.; Stockton Press: New York, 1991, pp 309–331). The favorable properties of alginate, including non-immunogenicity, hydrophilicity, and relatively low cost have prompted attempts to use this material as wound dressing, dental impression, and immnobilization scaffolds for cultured and transplanted cells (Gombotz et al., Protein release from alginate matrices. Adv. Drug Deliv. Rev. 1998, 31, 267–285; Shapiro et al., Novel alginate sponges for cell culture and transplantation. Biomaterials 1997, 18, 583–590). Alginate is considered to be a biocompatible polymer (Klock et al., Biocompatibility of mannuronic acid-rich alginates. Biomaterials 1997, 18, 707–713.), although contaminating factors may induce significant inflammation if the polymer is not suitably purified (Skják-Braek et al., Alginate as immobilization material. II: determination of polyphenol contaminants by fluorescence spectroscopy, and evaluation of methods for their removal. Biotech. Bioeng. 1989, 33, 90–94). Alginate hydrogels have been previously proposed for a number of drug delivery applications (Kikuchi et al., Pulsed dextran release from calcium-alginate gel beads. J. Control. Rel. 1997, 47, 21–29; Morgan et al., Alginates as drug carriers: covalent attachment of alginates to therapeutic agents containing primary amine groups. Int. J. Pharm. 1995, 122, 121–128; Murata et al., Additive effect of chondroitin sulfate and chitosan on drug release from calcium-induced alginate gel beads. J. Control. Rel. 1996, 38, 101–108). One disadvantage of alginate hydrogels is that they are not chemically broken down in mammals, e.g., because of the lack of alginase. They instead dissolve in an uncontrollable and unpredictable manner following the dissolution of calcium into the surrounding medium. Furthermore, the molecular weight of intact alginate is typically above the renal clearance threshold of the kidney thus preventing it from being excreted from the body (Al-Shamkhani et al., Radioiodination of alginate via covalently-bound tyrosinamide allows for monitoring of its fate in vivo. J. Bioact. Compat. Polym. 1995, 10, 4–13). Further, some of the limitations of hydrogels include the poor release profile of small molecules as well as low molecular weight polymers. The release of such compounds is typically diffusion controlled which results in an initial burst of the drug in a short time period. Limitations on the control of drug release makes hydrogels unsuitable for many types of drug delivery applications where different release profiles are desirable.

A related application, PCT/US97/16890, international filing date Sep. 17, 1997, describes modified alginates covalently coupled to molecules useful for cellular interaction. While the current invention is directed to different drug delivery applications and provides a detailed description of a particular manner of coupling of the drug, several aspects of the related application are applicable in achieving the current invention or are useful in combination with the current invention. The disclosure of PCT/US97/116890 is, therefore, incorporated by reference herein, as a whole.

Also in connection with PCT/US97/16890, it is another aspect of this invention that the PAG (poly(aldehyde guluronate)) materials and coupling chemistry described herein may be used for the cellular interaction uses described in the related application. For example, the PAG material herein could be used as the modified alginate and means for covalently coupling the molecules could be used for bonding the molecules for cellular interaction where those molecules have a functional group useful for such coupling or can be modified to provide such.

In one method for obtaining materials suitable for the invention, a natural or synthetically produced alginate or other polysaccharide is oxidized to convert at least a portion of the guluronate units to aldehyde guluronate units.

Natural source alginates, for example from seaweed or bacteria, are useful and can be selected to provide side chains with appropriate M (mannuronate) and G (guluronate) units for the ultimate use of the polymer. It is also preferred to use an alginate material of high guluronate content since the guluronate units, as opposed to the mannuronate units, provide sites for ionic crosslinking through divalent cations to gel the polymer. Isolation of alginate chains from natural sources for use as the side chains herein can be conducted by conventional methods. See *Biomaterials: Novel Materials from Biological Sources*, ed. Byrum, *Alginates* chapter (ed. Sutherland), p. 309–331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in Spaltro (U.S. Pat. No. 5,490,978) with other alcohols such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the alginate material is preferably conducted with a periodate oxidation agent, particularly sodium periodate, to provide the alginate with aldehyde groups, preferably poly(aldehyde guluronate) (PAG). The degree of oxidation is controllable by the mole equivalent of oxidation agent, e.g., periodate, to guluronate unit. For example, using sodium periodate in an equivalent % of from 2% to 100%, preferably 5% to 50%, a resulting degree of oxidation, i.e., % if guluronate units converted to aldehyde guluronate units, from about 2% to 70%, preferably 5% to 50%, can be obtained. The aldehyde groups provide functional sites for crosslinking and for bonding to a drug or prodrug. Further, oxidation of the alginate materials facilitates their degradation in vivo, even if they are not lowered in molecular weight. Thus, high molecular weight alginates, e.g., of up to 300,000 daltons, may be degradeable in vivo, when sufficiently oxidized, i.e., preferably at least 5% of the guluronate units are oxidized to aldehyde guluronate units.

Before, during or after the oxidation, the alginate material may be treated to provide a material of lower molecular weight, particularly at or below the renal threshold for clearance by humans. Preferably, the alginate or polysaccharide is reduced to a molecular weight of 1000 to 80,000 daltons, more preferably 1000 to 60,000 daltons. The reduction in molecular weight can be effected by hydrolysis under acidic conditions or by oxidation, to provide the desired molecular weight. The hydrolysis is preferably conducted in accordance with a modified procedure of Haug et al. (Acta. Chem. Scand., 20, p. 183–190 (1966), and Acta. Chem. Scand., 21, p. 691–704 (1967)), which results in a sodium poly(guluronate) of lower molecular weight which is essentially absent of mannuronic acid units. The oxidation to lower molecular weight is preferably conducted with a periodate oxidation agent, particularly sodium periodate; see PCT/US97/16890. Oxidizing commercially available high molecular weight alginates according to the invention, the average molecular weights and the aldehyde contents of the resulting materials can be readily controlled based on the oxidation conditions employed. Thereby, materials which can be eliminated from the body after degradation of the crosslinking therein can be provided. If the molecular weight lowering step is conducted by oxidation, the molecular weight lowering and oxidation step discussed above can be conducted as one step.

The oxidized and optionally molecular weight lowered alginate, for example a PAG material, is then crosslinked by a covalent crosslinking agent and optionally also by divalent cations. The covalent crosslinking agent provides two or more functional groups per molecule which are capable of degradeable covalent bonding to the aldehyde groups of the oxidized alginate. Preferred crosslinking agents are compounds with two or more hydrazide groups, particularly dihydrazides, more particularly adipic acid dihydrazide (AAD). The hydrazide group reacts with the aldehyde to provide a hydrazone bond which is hydrolyzable in vivo. The extent of crosslinking can be controlled by the concentration of crosslinking agent and the concentration of the oxidized alginate in aqueous solution; the higher concentration of either corresponding to a higher extent of crosslinking. Useful concentrations therefor are, for example, from 50 to 300 mM of crosslinking agent and from 5 to 10 wt % of oxidized alginate, e.g., PAG. The extent of crosslinking alters the mechanical properties of the gel and can be controlled as desired for the particular application; see PCT/US97/16890. In general, a higher degree of crosslinking results in a stiffer gel having a lower degradation rate.

Without oxidation, optionally molecular weight lowering and crosslinking, alginate hydrogels have limited mechanical properties and their degradation cannot be readily controlled. They dissolve in an uncontrollable manner upon loss of divalent cations and release high and low molecular weight alginates. The high molecular weight non-oxidized degradation products are not readily broken down in mammals and are slow to clear from the body.

The reaction from guluronate alginate units (1) to aldehyde guluronate (PAG) units (2) and then crosslinking by adipic dihydrazide (AAD) to crosslinked PAG (3) is exemplified in Equation 3 in Example 1.

Either during or after covalent crosslinking, ionic crosslinking of the oxidized alginate through divalent cations, particularly calcium, can also be conducted. Such crosslinking is effected with oxidized alginates, e.g., PAG, in a similar manner to alginates or other modified alginates; see PCT/US97/16890. Such crosslinking will also alter the mechanical properties and can be used if desired depending on the particular application.

Also, either before or during covalent crosslinking and/or ionic crosslinking of the oxidized alginate, the drug or prodrug is bonded to the hydrogel. Drugs which have a functional group capable of providing a degradeable covalent bond directly to the aldehyde groups of the oxidized alginate can be coupled to the hydrogel thereby. Further, drugs which have a functional group capable of providing a degradeable covalent bond to a linking compound which linking compound has a further functional group capable of providing a degradeable covalent bond to the aldehyde groups of the oxidized alginate can be coupled to the hydrogel. See, e.g., Heindel et al., *Bioconjugate Chemistry*, vol. 1, p. 77–82 (1990). In this case, hydrolysis of the bond between the drug and linking compound will release the active drug, while, hydrolysis of the bond between the linking compound and the oxidized alginate will provide a prodrug which will not be active until the bond between the drug and linking compound is hydrolyzed. Providing a prodrug in this manner may be advantageous in certain controlled release applications. Also, drugs which can form ionic bonds with the oxidized alginate hydrogel can be coupled thereby.

Thus, for example, drugs with a hydrazide group can be degradeably covalently bonded directly to the oxidized alginate, particularly PAG. However, because few drugs have hydrazide groups, the more applicable means of providing a degradeable covalent bonding of the drug is to react a drug having an aldehyde or ketone functional group with a compound having one or more hydrazide groups, particularly dihydrazides such as adipic acid dihydrazide (AAD), to provide a structure wherein there is degradeable covalent hydrazone bond between PAG and AAD and between AAD and the drug. See, e.g., Example 1 herein. As described above, hydrolysis of the bond between the drug and AAD will release the active drug, while, hydrolysis of the bond between AAD and the PAG will provide a prodrug which will not be active until the bond between the drug and AAD is hydrolyzed.

Drugs which have a positively charged ionic group may exhibit ionic bonding to the hydrogel through affinity with negatively charged carboxylate groups on guluronate units remaining in the oxidized alginate. Particularly, drugs with positively charged amine or ammonium groups may be carried by the hydrogel through ionic bonding.

Drugs which do not have the functional groups suitable for degradeable covalent bonding or ionic bonding will still exhibit some extent of controlled release from the hydrogels of this invention due to the need for the drug to diffuse from the hydrogel. But such diffusion controlled release does not provide as much control as the bond degradation effects described above.

This invention further contemplates any combination of the above bonding and other controlled release effects to fulfill the needs of a particular application. As described above, many variables are adjustable to tailor the mechanical properties of the carrier to the particular ultimate utility. Further, the different means of carrier-drug combination can be used, for example, to provide release of the same or different drugs by different mechanisms (e.g., covalent bond degradation, ionic bond degradation and diffusion control) from the same gel carrier or different gel carriers used in combination.

As described above, a second part of this invention involves modifying polymers, such as poly(vinyl alcohol) (PVA) and polyacrylamides, so that they can reversibly bind multiple molecules of drug per molecule of polymer. Any polymer which is biocompatible, water-soluble, preferably of less than 80,000 dalton molecular weight and can be bonded by a degradeable covalent bond to a drug, can be used. The conjugate of drug and polymer can be injected as a prodrug which will give a sustained release of active drug over time, i.e., as the degradeable bond hydrolyzes. This method can be used as a means to decrease the toxicity of the free drug, economize on the amount of drug given by increasing circulation time, and help to solubilize hydrophobic drugs. For example, because the active form of the drugs are released over time, the concentration of the active form of the drug at any given time can be minimized to levels where it is not substantially detrimental to certain organs. Further, conjugation with the polymer can be used to prevent a large portion of the drug from being eliminated through the kidneys before it has been able to act on the desired area. Additionally, these polymers can be used as cross-linkers for the oxidized alginate and poly(aldehyde guluronate) materials discussed above to form hydrogels. These polymers could be used to incorporate drugs and cross-link oxidized alginate and poly(aldehyde guluronate) simultaneously. The advantage over bifunctional cross-linkers is that a higher concentration of drugs could be incorporated into the same volume of gel.

Molecular weight of the backbone may be adjusted to achieve different average circulation times. For example, the molecular weight preferably ranges from 500 to 80,000. There are several different classes of drugs and types of applications which are well suited to this invention.

The linking of the polymer to the drug can be carried out through any of a number of chemistries which will provide a degradeable covalent bond between the polymer and the drug or a prodrug which is degradeably covalently bonded to release the active drug. For example, polymers which contain pendant carboxylic acid groups or can be modified to contain such groups can be transformed to hydrazides, e.g., by reaction with t-butyl carbazate followed by acid hydrolysis. The pendant hydrazide groups can then be reacted with drugs having an aldehyde or ketone functional group to provide a degradeable hydrazone bond. Similarly, excess hydrazine and a carbodiimide, e.g., EDC or DCC, can be used to provide a hydrazide functional group for linking. See PCT/US97/16890 further regarding the carbodiimide chemistry. Carbodiimidazole is another activator that can be utilized to couple amines, carbazides and hydrazides to carboxylic acid groups. The length of the pendant group in these polymers can also be controlled by using adipic dihydrazides (as well as other dihydrazides) to couple with the activated carboxylic acids in a manner similar to that described above for the hydrogels.

All drugs containing aldehyde and/or ketone groups could potentially be coupled to these modified polymers through the pendant hydrazide groups. The drugs may be coupled via the formation of a hydrazone bond between the drug and the carrier. The polymeric drug carrier is water soluble and could be administered by injecting aqueous solutions of the carrier intravenously. The drug is then released by the slow hydrolysis of the hydrazone bond. The linkage of the drug Taxol to poly(vinyl alcohol) modified with succinic anhydride, for example, is shown in the following equation.

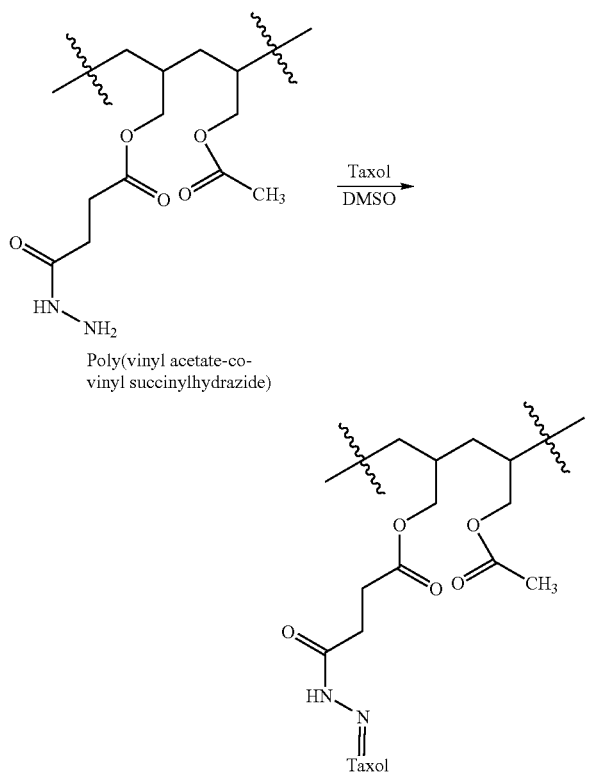

Equation 1

The linkages between the hydrazide groups and PVA is through ester bonds which are known to be degradeable. After degradation of the ester bonds in the polymeric carrier (see equation below), PVA is expected to be cleared from the body due to its low molecular weight.

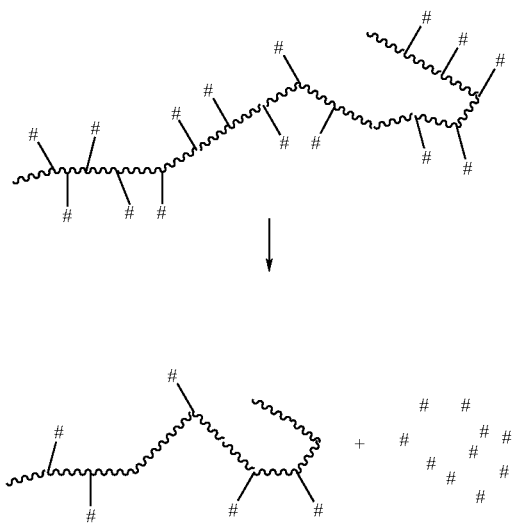

Equation 2

Water soluble polymeric drug carriers have been extensively investigated to deliver anti-neoplastic agents for several reasons. Some drugs, such as paclitaxel, have low solubility in aqueous solutions. By incorporating these drugs in a water soluble polymer, the solubility of the drug in aqueous solutions can be enhanced. Other advantages of such an application include increasing the half life of drugs in the blood stream when administered intravenously. For example, by utilizing a polymeric drug carrier of high molecular weight, the rate of clearance of the carrier is expected to be much slower than the clearance of small drug molecules. Polymeric drug carriers can also be designed to release drugs in a sustained manner, which in turn eliminates the need for frequent intravenous administration of these drugs. This may also decrease the cytotoxicity of these agents. Even though the circulation half life of the carrier is high in the blood stream, the circulation half life of the free drug remains low, and it is at a much lower concentration than the prodrug at any given time.

Although not intending to be limiting upon the potential applications of the invention, some specific applications for the hydrogels and/or water-soluble polymers, which also further illustrate the invention, are provided below.

Cancer is the second leading cause of death in the United States today and thus draws a good fraction of the resources of the health care industry. A large portion of cancer research is focused on finding new ways to deliver existing anticancer drugs in more efficient treatments. Today many cancers are treated with chemotherapy, where the patient receives large doses of anticancer drugs intravenously. Unfortunately, these anticancer drugs are highly toxic and cause wide spread systemic damage to the patient in addition to killing the tumor. A variety of materials had been utilized to incorporate drugs and deliver them in a controlled manner over a wide range of time frames. These materials include synthetic and natural polymers formulated as nanoparticles, microspheres, biodegradable polymeric disks, liposomes, inclusion complexes, and hydrogels (Ulbrich et al., "Synthesis of novel hydrolytically degradable hydrogels for controlled drug release" *J. Control. Rel.* 1995, 34, 155–165; and Draye et al., "In vitro release characteristics of bioactive molecules from dextran dialdehyde cross-linked gelatin hydrogel films" *Biomaterials* 1998, 19, 99–107). According to the invention, cross-linked oxidized alginate hydrogels can be used as an injectable drug delivery carrier for drugs. Drugs such as daunomycin and doxorubicin can be incorporated into the hydrogel via covalent attachment. Mitoxantrone and cisplatin, for example, were incorporated via the ionic complexation of these drugs onto the alginate backbone. Methotrexate, for example, can be physically entrapped into the hydrogel. Thus, the hydrogels can provide controlled release on the basis of the degradeable covalent linking effect, degradeable ionic bonding effect and diffusional effect from the gel, as well as by the degradation of crosslinking and ionic gelling of the gel itself. For example: Methotrexate was quantitatively released from the hydrogels within 5 days at all conditions by diffusing out from the gel; and a wide range of release profiles was observed with mitoxantrone and doxorubicin infused hydrogels depending on the concentration of covalent and ionic cross-linkers. The duration of the release of these to drugs could be controlled from as little as 2 days to greater than 3 months, for example.

Also because of the side effects of chemotherapy drugs, including nausea, weight loss, hair loss, severe immune suppression, myelosuppression (e.g., bone marrow depression), nephrotoxicity, gastrointestinal disturbances and cardiotoxicity, it would be desirable to provide localized delivery whenever possible to minimize these effects. For example, this may be the case in the following instances: 1) the tumor(s) are confined to a relatively small area (e.g. the peritoneal cavity), 2) the tumor is inoperable (e.g. some brain cancers), or 3) following removal of a tumor which does not appear to have metastasized to kill any cells that might not have been removed (e.g. following lumpectomy of breast cancers). Several types of currently approved chemotherapy drugs would work well using the delivery systems of the invention in such a manner. For example, anthracyclines such as daunomycin, doxorubicin, epirubicin and idarubicin contain a ketone functional group which can be reacted with the above-described modified hydrogels to form a controlled release drug-carrier combination with a degradeable hydrazone bond. Others drugs which contain amine groups, such as mitoxantrone, interact ionically with the hydrogel and also can provide a gradual release over time. Other chemotherapy drugs which may be suitable to the inventive carrier systems include: bleomycins and mitomycins which have amine groups, plicamycin which has ketone groups, and platinum complexes which have amine groups. Other drugs which may be developed or are in clinical trials and which have similar structural features may be useful with the described carriers.

Paclitaxel (TAXOL) and docetaxel (TAXOTERE) also contain ketones and can be covalently linked to the modified hydrogels. These and other water insoluble drugs may be suitable for diffusion controlled release as well.

Other types of cancer, where the tumor has metastasized or where the cancer is widespread, such as in leukemia, require systemic chemotherapy or other treatment to eliminate cancer cells throughout the body. In these cases, prodrugs may be advantageous over delivery of free drug to reduce toxicity to the heart, blood vessels, immune system, etc., as well as to lengthen circulation time of the drug. For example, it has been shown that systemic delivery of TAXOL may be more effective against Kaposi's sarcoma when given over a 96 hour period intravenously instead of over 3 hours (J. Clin Oncol, 1998, 16(3):1112–1121). In addition, solubilizing highly hydrophobic drugs such as TAXOL by binding to a suitable water-soluble polymer backbone will decrease side effects seen with current carriers. According to the manufacturer of TAXOL (Mead Johnson Oncology Products, a Bristol-Myers Squibb Co. Princeton, N.J.), the carrier for TAXOL is a 50/50 mixture of castor oil and ethanol which can cause anaphylaxis and severe hypersensitivity reactions in some patients which may be fatal. The previously mentioned anthracycline and other drugs which form covalent linkages to the modified alginates may also be used to form prodrugs.

TAXOL and TAXOTERE coupling to the hydrogel may also be used to prevent re-occlusion of arteries following angioplasty. Previous studies have demonstrated that TAXOL will inhibit smooth muscle cell proliferation and prevent neointima formation in rabbits following balloon angioplasty (Circulation, 1997, 96(2):636–645).

Other applications for this invention include localized or systemic delivery of growth factors. Particularly, vascular endothelial growth factor (VEGF) may be used for localized vascularization. Sustained slow release of growth factors will allow a greater or similar effect to be achieved with a much smaller amount of drug.

The hydrogel system is ideally suited to many types of steroid delivery as well. Gels are inexpensive, injectable and can be engineered to release the drug over a period of a few weeks to several months, for example. Progestin-only contraceptives are particularly well suited to this application. The progestin could be either covalently bound, such as progesterone, medroxy-progesterone acetate, norethynodrel, and hydroxyprogesterone caproate, or subject to diffusion release since the hydrophobic nature of these drugs (as well as others such as norgestrel, norethindrone, norgestimate, desogestrel and 19-nortestosterone which may not be chemically bound) would result in a slow release from the gel. The gels could be pre-formed and implanted or injected directly, making them versatile and easy to administer. An injectable sustained release system would be an improvement over the commercially available NORPLANT which requires implantation. In addition, they could easily be injected closer to the sight of action rather than in the arm, as with NORPLANT, reducing the amount of drug required. The gels are not easily removed; however, those designed for a limited period of delivery, such as a few weeks, could be used on a trial basis. This system would also provide a significant improvement over commercially available injectable progestin-only contraceptives such as DEPO-PROVERA (150 mg of medroxy progesterone acetate given by intramuscular injection every 3 months; Pharmacological Basis of Therapeutics, 9th Edition, Hardman and Limbird, Editors-in-Chief, McGraw Hill, 1996, p. 1432) because a sustained low level of the drug would be in the system at all times rather than in periodic very high concentrations. This would be a more efficient use of drug and should decrease side effects associated with this form of contraception. Other steroid applications include hormone replacement therapy using diffusion controlled release of estrogen and/or progesterone related compounds and release of cortisone or other suitable drugs to inflamed joints in rheumatoid arthritis.

The entire disclosure of all applications, patents and publications, cited above and below, is hereby incorporated by reference.

In the foregoing and in the following examples, all temperatures are set forth uncorrected in degrees Celsius; and, unless otherwise indicated, all parts and percentages are by weight.

EXAMPLES

Example 1

Alginate was hydrolyzed under acidic conditions to yield sodium poly(guluronate), 1, as a low molecular weight polysaccharide (5000 daltons), following a modified procedure of Haug et al., cited above. The purity of this product was assessed by both 1H-NMR and 13C-NMR, and both analysis indicated the complete absence of mannuronic acid in the product, as previously reported with this procedure. Penman et al., *Carbohyd. Res.* 1972, 25, 273–282; Boyd et al., *Carbohyd. Res.* 1978, 61, 223–226; and Grasdalen et al., *Carbohyd. Res.* 1981, 89, 179–191. Sodium poly(guluronate) was then oxidized by sodium periodate to form the poly(aldehyde guluronate) (PAG), 2. This reaction was monitored by the appearance of the aldehyde symmetric vibrational band (carbonyl) at 1735 $cm^{-1}$ via FTIR. The poly(aldehyde guluronate) intermediate was then crosslinked with a homobifunctional cross-linker, adipic dihydrazide, to form hydrogels, 3. This coupling reaction was followed by the disappearance of the aldehyde symmetric vibrational band and the appearance of a carbonyl band for the hydrazide at 1639 cm$^{-1}$. The reactions are illustrated by Equation 3:

and PAG. The hydrolysis of the linkage between AAD and the drug will result in the release of the free and active drug. On the other hand, the hydrolysis of the linkage between AAD and PAG will release the drug coupled to AAD.

This is the inactive form of the drug, which could be activated by hydrolyzing the linkage between AAD and daunomycin. Hence, when daunomycin is released with AAD, it is a prodrug.

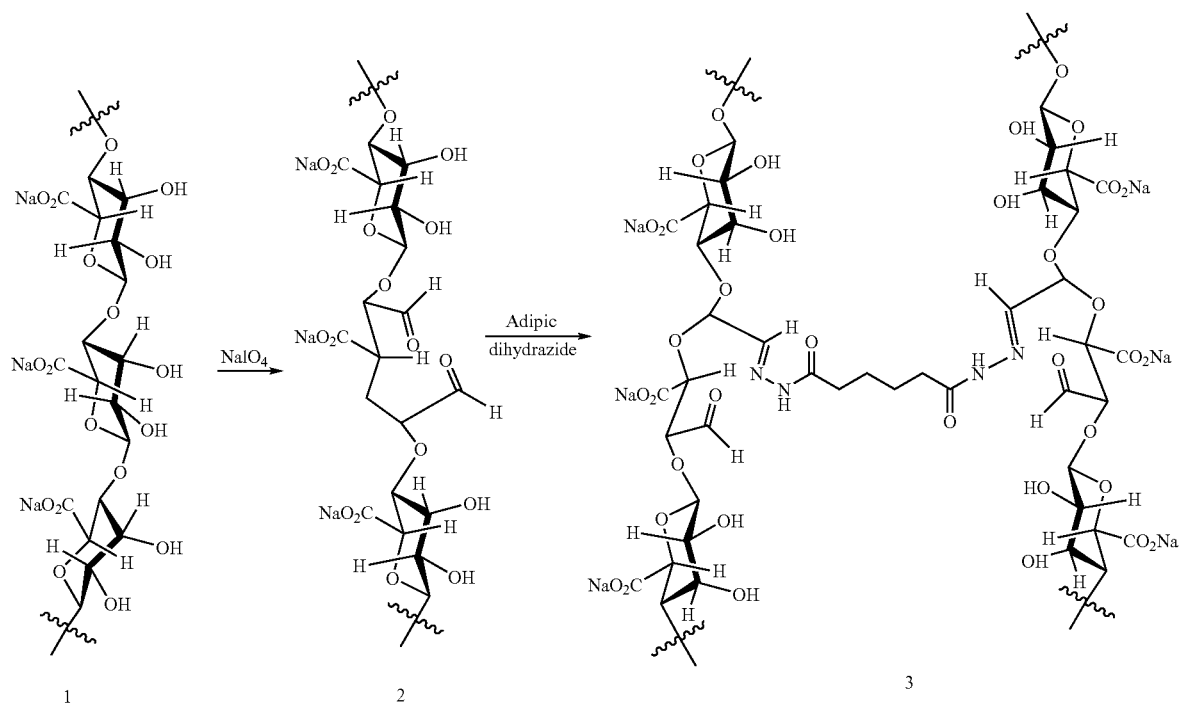

Equation 3

Example 2

In order to couple daunomycin to cross-linked PAG hydrogels, an aqueous solution of molar excess adipic hydrazide was mixed with aqueous daunomycin. One hydrazide terminal reacts with the drug to form a hydrazone bond, while the other terminal is free; see Equation 4. When this solution is added to PAG, the free hydrazide group covalently bonds the drug to the backbone of the polymer; see Equation 5. The hydrazide group on daunomycin reacts with one aldehyde group on the backbone of the polymer to form a labile hydrazide bond. The rest of the adipic dihydrazides cross-link the PAG to from a hydrogel. The mechanism of the release of the drug from the gel is via chemical hydrolysis of either the hydrazone bond between the drug and adipic dihydrazide or the hydrazone bond between AAD

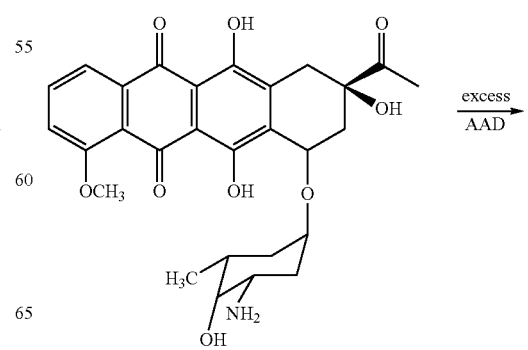

-continued

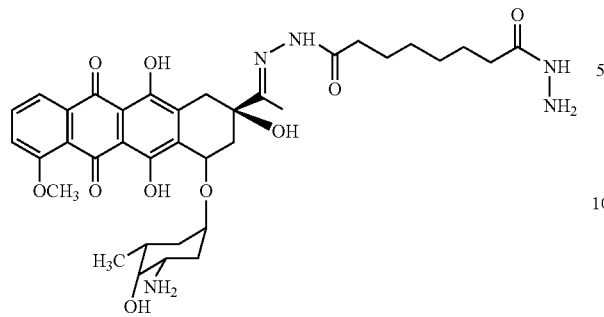

Daunomycin

Equation 4

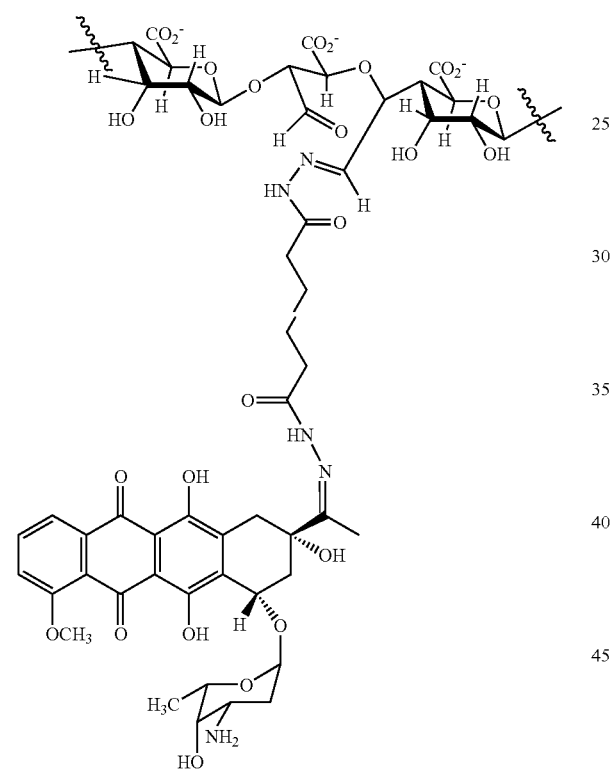

Equation 5

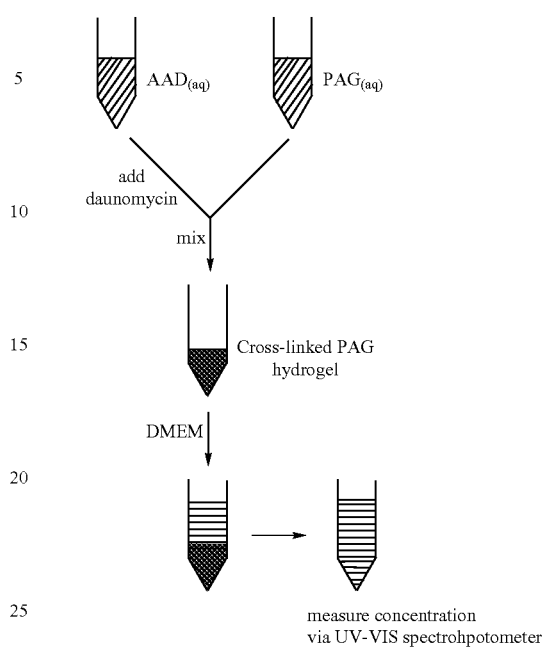

Example 3

As shown in the following diagram, daunomycin was dissolved in an aqueous solution of adipic dihydrazide (0.5 mM). Aqueous solutions of PAG (20 wt %) were mixed with aqueous solutions of daunomycin and AAD in a 5 ml sterile tube. The solution was allowed to stand at room temperature for one hour during which the solution gelled. Dulbecco's Modified Eagle's Medium (DMEM) containing penicillin and streptomycin was added to each tube. The gels were then incubated at 37° C., and the medium was changed periodically. The released drug was quantified spectrophotometrically at 480 nm wavelength using a UV-VIS spectrophotometer.

A typical release profile of daunomycin from cross-linked PAG hydrogels is shown in FIG. 1. PAG (6 wt %) containing 8 mM daunomycin was cross-linked with 150 mM AAD. A linear release of 1% drug per day was seen during the first ten days followed by approximately 4% per day for the following twenty-two days. The total amount of incorporated daunomycin was released within thirty days of incubation when the matrix completely dissolved in the media.

Example 4

In the next set of experiments, 6 wt % PAG was cross-linked at various concentrations of adipic dihydrazide and the release of drug was monitored spectrophotometrically. The total amount of drug loaded in the gels was released in two days when 50 mM of the AAD cross-linker was used. As the concentration of cross-linker was increased, the rate of release of daunomycin decreased. Total drug was released in two weeks at 100 mM AAD and in more than six weeks at elevated AAD concentrations; see FIG. 2. It is important to note that at low concentrations of adipic dihydrazide the complete release of daunomycin was accompanied by the complete dissolution of the hydrogel. Hydrogels with low cross-link density degrade at a faster rate

Example 5

In addition to covalent cross-linking, ionic cross-linking decreased the release rate of daunomycin as seen in FIG. 3. In the absence of calcium, all the incorporated drug was released in four weeks. At 40 mM calcium ion concentrations only 40% of the drug was released during the first six weeks at a rate of 0.8% drug per day. The release rate of daunomycin can, thus, be additionally controlled by varying the concentration of calcium in the hydrogels. The presence of calcium within the hydrogel increases the number of ionic cross-links, as with natural alginate. This results in a hydrogel with high mechanical strength with slower degradation rate and lower water content. This may decrease the rate of drug diffusion as well as the rate of drug that is chemically released from the gel.

Example 6

In the next series of experiments, we examined the effect of the PAG concentrations on the release of daunomycin. In the presence of ionic cross-linking with calcium, no difference was observed between 6, 7, and 8 wt % PAG during the first 48 days (FIG. 4). However, we expect that the release of the drug will vary at the end of the release period due to the difference in the degradation rates of these gels. In comparison, there was a significant difference in the release profiles of daunomycin in the absence of ionic cross-linking by calcium.

Example 7

We have formed hydrogels at 6 wt % PAG and cross-linked at 150 mM AAD in the absence of calcium. These gels were loaded with daunomycin at various concentrations. As the concentration of daunomycin was increased, the percentage release of daunomycin decreased (FIG. 5). This indicates clearly that the mechanism of release is not diffusion controlled but rather due to the chemical hydrolysis of the linkage between daunomycin and the polymer. This is confirmed when the amount of daunomycin released from all hydrogels is measured and no difference in the release profile was noted at different concentration of the drug (FIG. 6).

Example 8

The activity of covalently bound daunomycin released from 6 wt % PAG gels was tested using KB cells in a standard cytotoxicity assay. Gels containing either zero, 13.3 or 30 mg of drug per gram of PAG were incubated in sterile media at 37° C. which was tested and replaced weekly. Activity was compared with free drug which had an $IC_{50}$ of 0.04 µM and a daunomycin/AAD prodrug mixture (100 fold excess of AAD) with an $IC_{50}$ of 0.5 µM. A typical example of results obtained from this assay are shown in FIG. 7 where daunomycin released during the second week of incubation was tested. The material released from non-daunomycin containing gels had no adverse effect on cell growth. $IC_{50}$ values (FIG. 8) for the released daunomycin were initially higher than that seen with the AAD/daunomycin prodrug mixture; however, they dropped to a value between that seen for free daunomycin and the prodrug by the second week of release.

Example 9

A second type of anthracycline was used to determine whether the AAD bound to the quinone group of daunomycin in addition to the ketone. Mitoxantrone contains only the quinone group (see formula below) and was not found to form a prodrug when mixed with AAD as shown in FIG. 9.

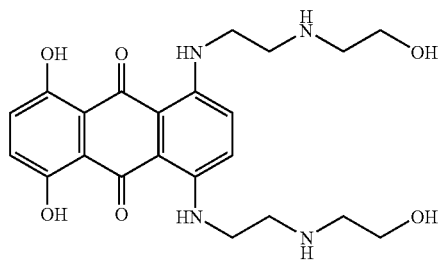

Example 10

Diffusion release of water soluble compounds was studied using the dyes Brilliant Blue R and G as models of compounds which have no functional group for covalent bonding. Samples containing 9.8, 19.5, and 39.1 mg brilliant blue per gram of PAG either with or without calcium (which enhances gelling) were studied over a period of several weeks. In contrast to chemically bound compounds, the majority of the Brilliant Blue dyes added was released within a few days, and the amount released was in direct proportion to the amount incorporated. The presence of calcium had no effect on release. See FIG. 10.

Example 11

Angiogenic drugs have been identified which induce vascularization in vivo (e.g., vascular endothelial growth factor, VEGF). Vascularization of engineered tissues is an essential step in the development of these tissues. A typical release profile of VEGF from cross-linked PAG hydrogels prepared according to the following diagram is shown in FIG. 11. An initial burst of around 45% of the drug during the first two days is followed by a sustained release of 1% drug per day for the following 25 days. In the presence of heparin/sepharose gel within the matrix, a slower initial burst was seen. Less than 15% of the drug was released during the first two days followed by a sustained release of 1% drug per day for the next 25 days.

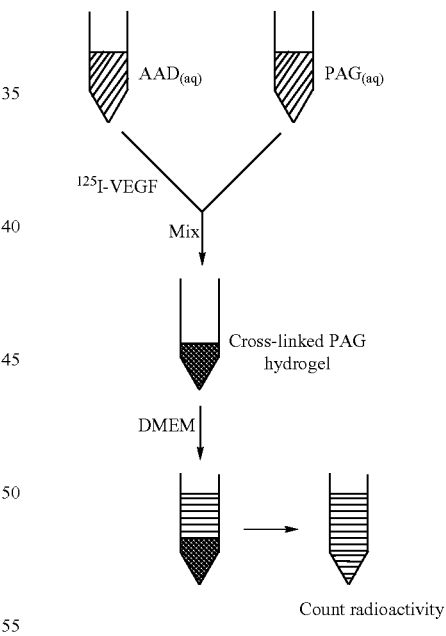

Example 12

The presence of heparin-sepharose beads decreased the rate the release of VEGF from the cross-linked PAG hydrogels. However, these beads cannot be used in biomedical applications because they are not biodegradable. Therefore, to mimic their effect, heparin was coupled to the backbone of PAG polymers. A water soluble carbodiimide, EDC, was used to activate the carboxylate groups in heparin. Excess AAD was then added to this solution, where one hydrazide group of AAD reacted to the activated carboxylates to form a stable bond. The other terminal of the AAD remained free and was used to anchor the heparin molecule to PAG. See Equation 6:

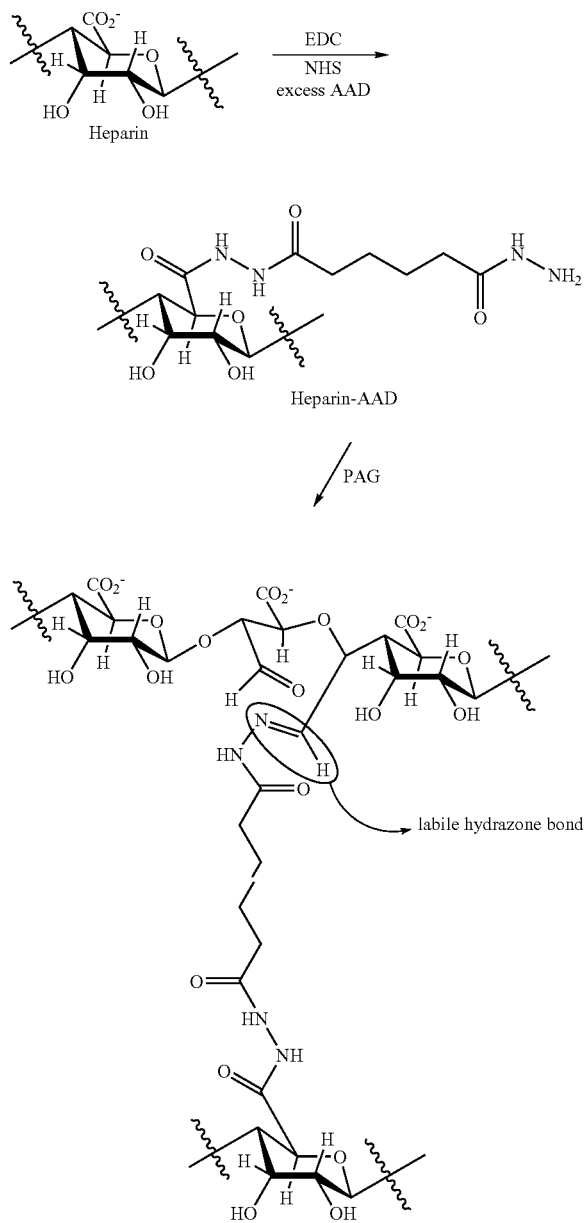

Equation 6

To prevent the deactivation of VEGF by PAG, a mixture of heparin and heparin-AAD was combined with an aqueous solution of VEGF and incubated overnight at room temperature. An aqueous solution of PAG was then added, and the mixture was allowed to gel for one hour. The release of VEGF from PAG hydrogels was 7% VEGF per day for the first three days followed by approximately 1% VEGF per day for the next 17 days which was similar to that obtained for heparin sepharose beads, except the delivery device remained biodegradable. See FIG. 12.

Example 13

The biocompatibility of PAG has been tested in vitro. In vitro tests using a standard cytotoxicity assay with KB cells showed that PAG in solution had no significant effect on cell growth over the range of concentrations tested (up to 600 µM PAG with an average molecular weight of 6200 g/mol) as shown in FIG. 13. AAD, the material used to covalently cross-link and bind drug to the PAG, did not adversely affect cell growth either over the concentration range tested.

Example 14

A similar type of release could be obtained from partially oxidized alginates. This would eliminate the necessity to hydrolyze alginates and give greater control over the molecular weights of these polymers. The molecular weights of partially oxidized alginates decreased with increasing concentrations of sodium periodate in the oxidation reactions (FIG. 14). When using 20% periodate and higher, the molecular weights of the resulting polymer were lower than the renal threshold for clearance in humans (80,000 daltons). As a result these polymers would be biodegradable and could potentially be used to incorporate and deliver drugs. Control over the molecular weight should provide another means of tailoring the properties of cross-linked alginates to optimize release of drugs for different applications.

Example 15

A polymeric drug carrier of interest has been synthesized from poly(vinyl alcohol). A solution of poly(vinyl alcohol) in N-methyl pyrolidone was allowed to react with succinic anhydride in the presence of N,N-dimethyl pyridine to form poly(vinyl acetate-co-vinyl succinate). The carboxylic acid pendant groups were then transformed to hydrazides by coupling t-butyl carbazate followed by acid hydrolysis. The pendant hydrazide groups could then be used to anchor drugs to the polymer. In a similar procedure, poly(vinyl acetate-co-vinyl succinate) was derivatized in one step using excess hydrazine and EDC chemistry. See Equation 7:

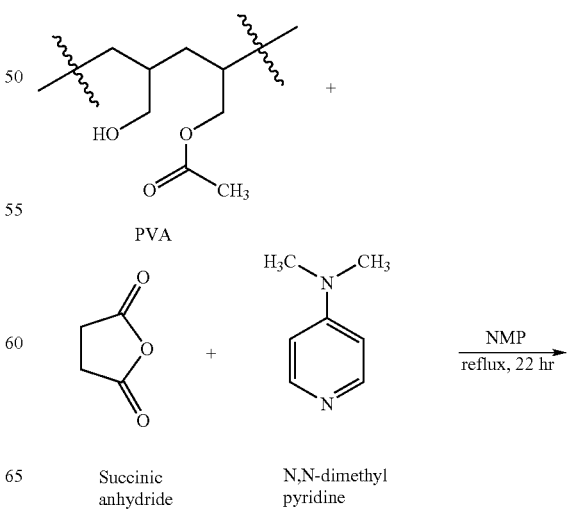

compound. The t-butyl protecting group can be hydrolyzed with trifluoroacetic acid to form a carbazide terminal group. See Equation 8. Drugs containing aldehyde and/or ketone groups can then be coupled to the dendrimer via the carbazide group in a similar manner to hydrazide groups. Drugs are released from the carrier through chemical hydrolysis of the carbazone bond.

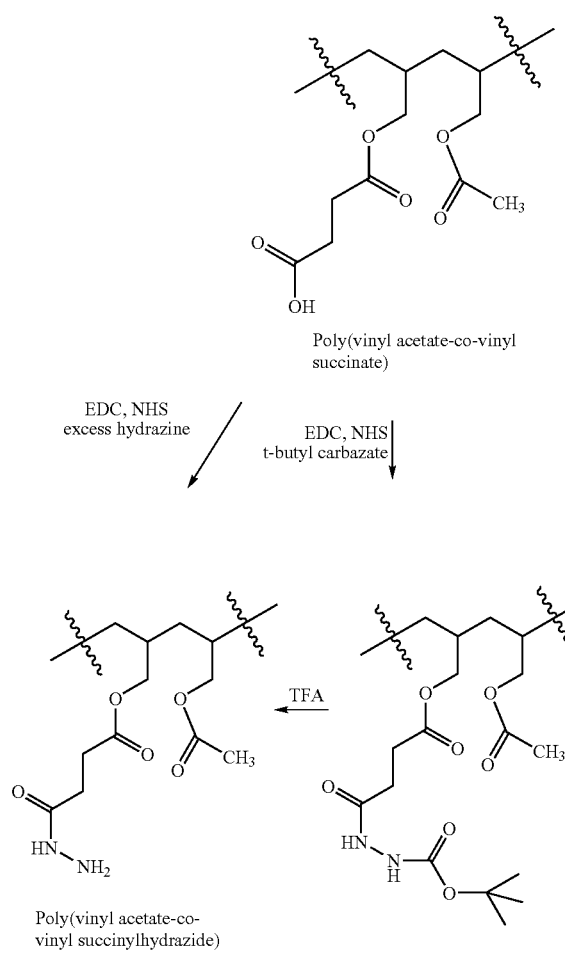

Equation 7

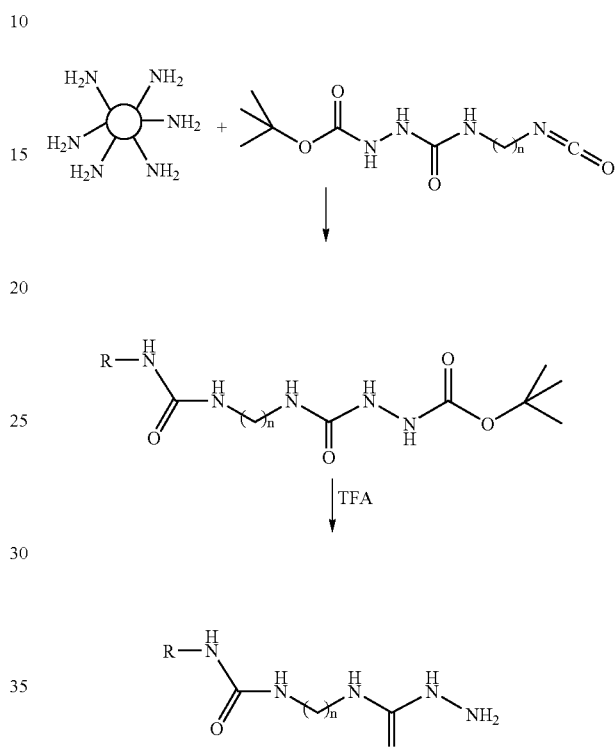

Equation 8

Example 16

Water soluble polymeric drug carriers can be synthesized from commercially available polyamine dendrimers. The amine terminals of these dendrimers can be functionalized by allowing the dendrimers to react with a monoisocyanate

Example 17

Poly(ethylene glycol) dendrimers can be synthesized starting with poly(ethylene glycol), PEG, using carbodiimide chemistry. See Equation 9. The amine groups in the dendrimer can be transformed to reactive hydrazide groups as in the previous example.

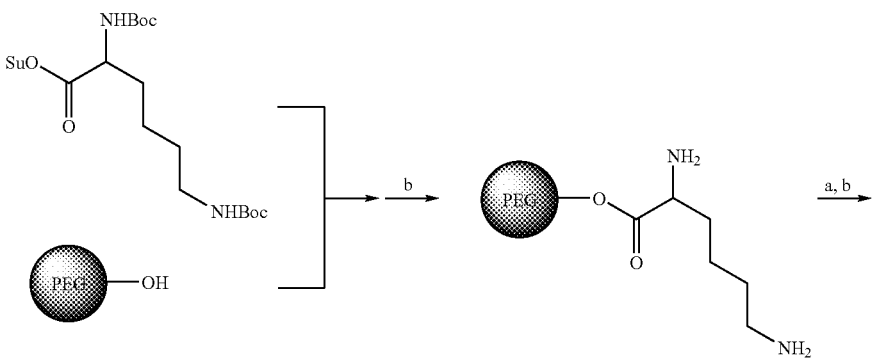

-continued
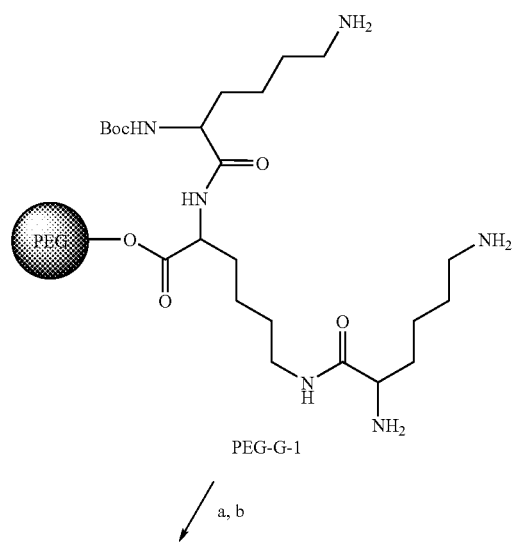
PEG-G-1
a, b
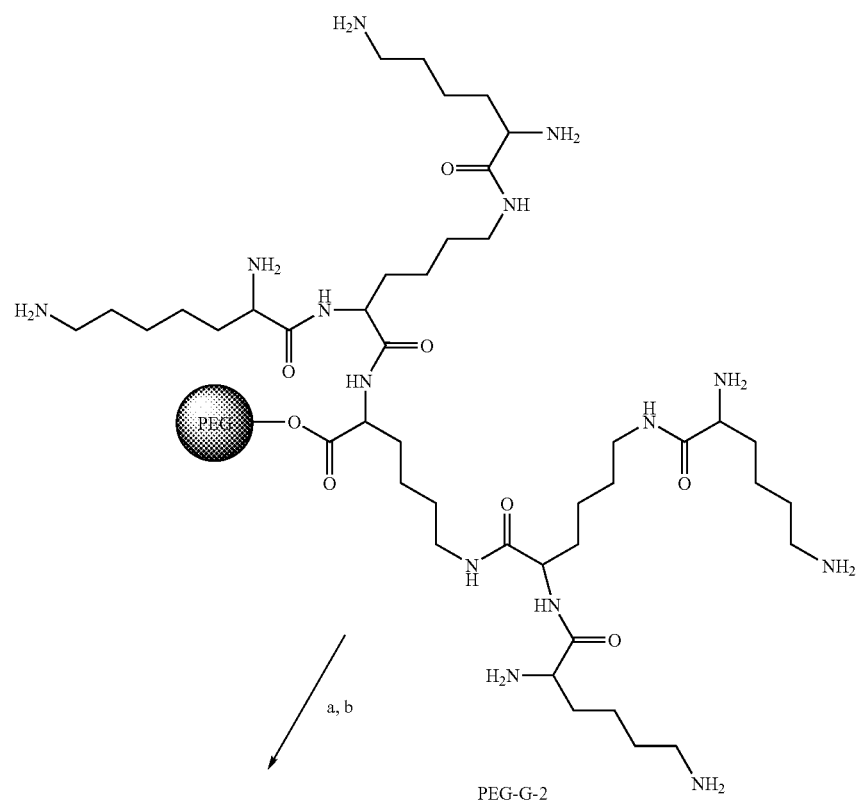
PEG-G-2
a, b

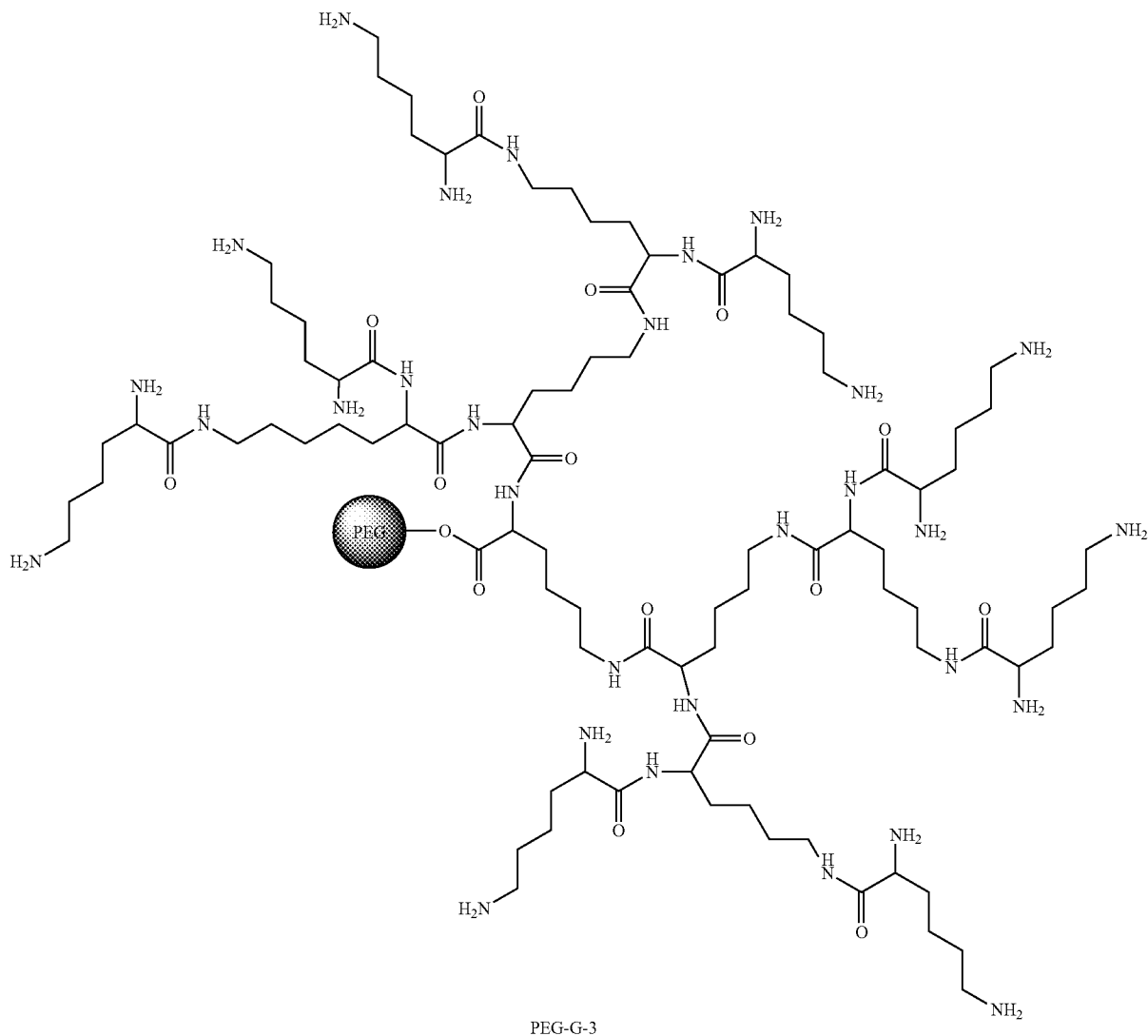

PEG-G-3

Equation 9: (a) DiBoc-lysine, DCC, HOBT, CH$_2$Cl$_2$ b) Trifluoroacetic Acid

Example 18

A similar approach can be used for the modification of poly(allylamine) and poly(vinylamine) by reacting them with succinic anhydride followed by hydrazide incorporation using carbodiimide chemistry to form poly-N-allyl- or vinyl-succinamidohydrazides. See Equations 10 and 11. As in the previous example, the reactive hydrazido groups provide a means to incorporate drugs to the polymer backbone via the pendant hydrazide. In contrast to the PVA-based materials, the amide bond formed between the poly(allyl amine) and the succinate group is a non-degradable bond.

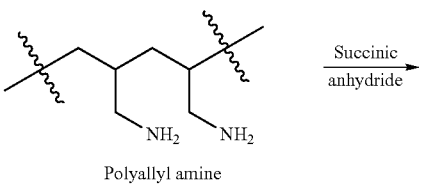

Polyallyl amine

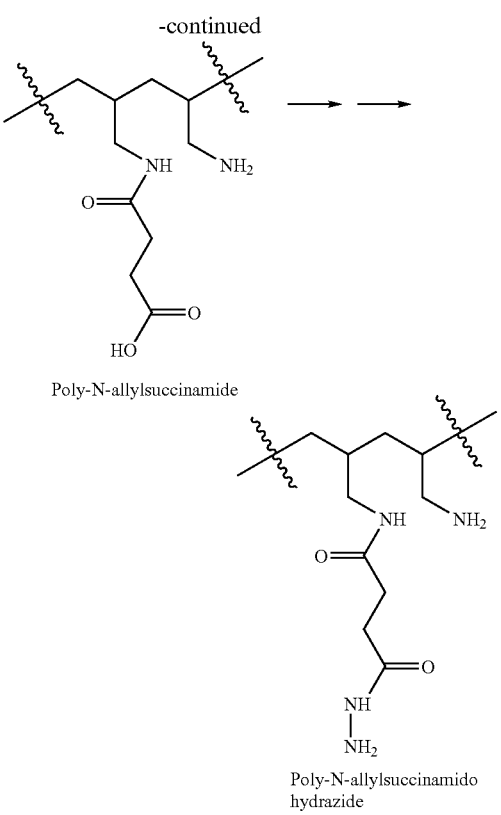

Equation 10: Synthesis of Hydrazido Derivatives of Poly(allyl Amine).

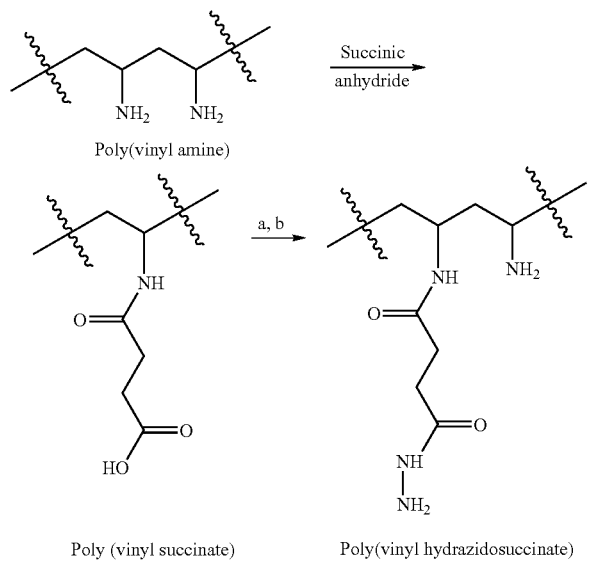

Equation 11: a) DCC, HOBT, t-Butyl Carbazate b) Trifluoroacetic Acid.

Example 19

In a further example for preparing oxidized alginate, aqueous solutions of sodium alginate were oxidized in the dark with sodium periodate at room temperature following a modified procedure reported previously (Painter T, Larsen B. Formation of hemiacetals between neighboring hexuronic acid residues during the periodate oxidation of alginate. Acta Chem Scand 1970; 24: 813–833). The amount of sodium periodate used in these reactions was varied in order to form alginates with different degrees of oxidation. The products were characterized with FTIR, where a peak was detected at 1730 cm$^{-1}$ corresponding for the symmetric vibrational band of aldehyde groups (FIG. 15). The degree of oxidation was determined by measuring the percentage of sodium periodate that was consumed in each reaction. Sodium periodate was almost quantitatively consumed in all conditions except when 100 percentage equivalents was used (Table 1). In this case, only sixty nine percent of periodate was consumed after 24 hours.

TABLE 1

Experimental degree of oxidation as a function of the percentage equivalents of sodium periodate. Reactions were run at a concentration of 0.8% w/w alginate in the dark at room temperature for 24 hours.

| Periodate Equivalents (%) | Periodate Consumed (%) | Degree of Oxidation |
| --- | --- | --- |
| 5 | 98.90 ± 0.22 | 4.94 |
| 10 | 98.87 ± 0.03 | 9.88 |
| 25 | 98.80 ± 0.02 | 24.70 |
| 50 | 98.69 ± 0.04 | 49.34 |
| 100 | 69.23 ± 2.06 | 69.23 |

Example 20

It is well known that polysaccharides are depolymerized under the conditions of the periodate oxidation (Painter T. J., Control of depolymerisation during the preparation of reduced dialdehyde cellulose; Carbohyr. Res. 1988; 179: 259–268). This depolymerization reaction could potentially yield oxidized alginates with low molecular weights. This is very attractive for biomedical applications of alginate derivatives since polymers with molecular weights lower than 80 kDa are expected to be cleared from the body in a similar manner to molecular weight alginate (Al-Shamkhani et al., Radioiodination of alginate via covalently-bound tyrosinamide allows for monitoring of its fate in vivo; J. Bioact. Compat. Polym. 1995; 10: 4–13). To investigate this, a series of experiments were carried out by varying the total amount of periodate used in each reaction. The molecular weight distribution of oxidized alginates was analyzed by aqueous gel permeation chromatography. Representative chromatograms of alginate and oxidized alginates as detected by the differential refractive index detector are shown in FIG. 16. The weight-average molecular weight of oxidized alginate was found to depend on the amount of sodium periodate used in each reaction. The weight-average molecular weight of the starting alginate was 394 kDa. Alginate oxidized with 5 equivalents of sodium periodate formed a polymer with a weight-average molecular weight of 198 kDa (Table 2):

TABLE 2

Molecular weight distributions of alginate and oxidized alginates.

| NaIO$_4$[1] (%) | Mw (kDa) | Mn (kDa) | Mz (kDa) | Pd (Mw/Mn) | IVw (dl/g) | F(x)[2] |
| --- | --- | --- | --- | --- | --- | --- |
| 0 | 358 | 130 | 650 | 2.75 | 9.40 | 12.5 |
| 2 | 198 | 113 | 284 | 1.76 | 5.60 | 19.9 |
| 5 | 147 | 69 | 251 | 2.13 | 3.44 | 35 |
| 10 | 94 | 48 | 156 | 1.95 | 1.73 | 58 |
| 20 | 69 | 35 | 114 | 1.99 | 0.91 | 61 |

TABLE 2-continued

Molecular weight distributions of alginate and oxidized alginates.

| NaIO$_4$[1] (%) | Mw (kDa) | Mn (kDa) | Mz (kDa) | Pd (Mw/Mn) | IVw (dl/g) | F(x)[2] |
|---|---|---|---|---|---|---|
| 50 | 46 | 27 | 67 | 1.67 | 0.39 | 83 |
| 100 | 29 | 17 | 45 | 1.75 | 0.40 | 96 |

[1]This number represents the percentage equivalents of sodium periodate initially added to the reaction mixture.
[2]F(x) is the weight fraction of the polymer with a molecular weight below 80 kDa.

The weight-average molecular weight then decreased as the percentage equivalents of periodate was increased to reach 26 kDa with 100% equivalents of sodium periodate. The same trend was observed with the number-average molecular weight and the z-average molecular weight which decreased from a value of 125 and 650 kDa respectively for alginate to 16 and 45 kDa for alginate that was oxidized with 100% equivalents of sodium periodate (Table 2). In addition, the intrinsic viscosity of the polymers decreased as periodate concentration was increased. This result is expected since the intrinsic viscosity of polymers is inversely dependent on the molecular weight distribution. To determine the fraction of each polymer that has a molecular weight below the renal clearance threshold (80 kDa), molecular weight distribution was evaluated. Only 12.5% weight fraction of the original unmodified alginate has a molecular weight below 80 kDa. This number increased to a value of 96% for alginates oxidized with 100 equivalents of sodium periodate (Table 2). As a result, we expect that 96% weight fraction of the alginate oxidized with 100 equivalents of periodate could be readily eliminated form the body via the kidneys in vivo applications.

Hydrogels were subsequently formed by the reaction of adipic dihydrazide and the oxidized alginates. The hydrazide group reacts with the aldehyde groups in oxidized alginate to form hydrazone bonds. Gels could be formed with solutions of oxidized alginate at 4% w/w and higher. The hydrogels were washed with water and soaked in double distilled water for 24 hours to eliminate the unreacted adipic dihydrazide. FTIR spectroscopic analysis of the dry hydrogels indicated the disappearance of the peak at 1730 cm$^{-1}$ that corresponds to the carbonyl stretching vibration of the aldehyde groups. Another band was detected at 1660 cm$^{-1}$ resulting from the carbonyl group of adipic dihydrazide (FIG. 15). However, the carbonyl band at 1660 cm$^{-1}$ is broad and overlaps with the carbonyl band at 1730 cm$^{-1}$, therefore, caution should be taken in interpreting this result as an indication of the complete consumption of the aldehyde groups in the gel.

The degree of swelling of cross-linked oxidized alginate hydrogels was analyzed after the hydrogels had reached the equilibration swelling in dd. water. The swelling ratio of these hydrogles varied significantly depending on the concentrations of both the ionic and the covalent cross-linkers (Table 3):

TABLE 3

Swelling ratio of cross-linked 6% w/w oxidized alginate in dd. H$_2$O as a function of the concentrations of the ionic and covalent cross-linkers.

| Adipic Dihydrazide (mM) | CaCl$_2$ (mM) | Swelling Ratio (49.7% | Swelling Ratio (90.3% oxidized) |
|---|---|---|---|
| 150 | 0 | — | 29.9 ± 1.2 |
| 150 | 5 | — | 29.2 ± 1.5 |

TABLE 3-continued

Swelling ratio of cross-linked 6% w/w oxidized alginate in dd. H$_2$O as a function of the concentrations of the ionic and covalent cross-linkers.

| Adipic Dihydrazide (mM) | CaCl$_2$ (mM) | Swelling Ratio (49.7% | Swelling Ratio (90.3% oxidized) |
|---|---|---|---|
| 150 | 10 | — | 29.6 ± 1.5 |
| 150 | 20 | 29.3 ± 0.4 | 17.7 ± 0.9 |
| 150 | 30 | 21.2 ± 0.7 | 14.7 ± 1.9 |
| 150 | 40 | 12.9 ± 0.2 | 11.7 ± 0.3 |
| 50 | 40 | 29.1 ± 0.1 | 20.1 ± 1.2 |
| 100 | 40 | 18.2 ± 0.6 | 13.1 ± 1.1 |
| 150 | 40 | 12.9 ± 0.2 | 11.7 ± 0.3 |
| 200 | 40 | 13.9 ± 0.3 | 11.8 ± 0.2 |
| 250 | 40 | 14.7 ± 0.3 | 12.4 ± 0.2 |

The swelling ratio of hydrogels made with 90% oxidized alginate and cross-linked at 150 mM adipic dihydrazide was 29.9±1.2 in dd. water. The swelling ratio then decreased with increasing concentrations of calcium to reach a minimum of 11.7±0.3 at 40 mM calcium ions. A similar trend was observed when the concentration of covalent cross-links was increased. The swelling ratio was 20.1±1.2 at 40 mM calcium ions and 50 mM adipic dihydrazide and decreased as the concentration of adipic dihydrazide decreased to reach 12.4±0.2 at 40 mM calcium ions and 250 mM adipic dihydrazide. The same trend was observed with 49.7% oxidized alginate, however, the swelling ratio was larger at all concentrations. This is expected because of the lower aldehyde content that results in a lower degree of cross-linking.

Example 21

To determine the efficiency of the cross-linking reaction in oxidized alginate hydrogels, hydrogels were formed at different experimental conditions and the compressive modulus was determined. We used the compressive modulus as a measure of the intermolecular cross-link density (Bouhadir et al., Synthesis of cross-linked poly(aldehyde guluronate) hydrogels. Polymer 1999; 40: 3575–3584). Several conditions were varied in a series of experiments, such as the concentration of the polymer, covalent cross-linker (adipic dihydrazide), and ionic cross-linker ($Ca^{+2}$). Cross-linked oxidized alginate hydrogels were first formed at different polymer concentrations. Alginate that was oxidized using 100% equivalents of periodate formed gels at 4% w/w polymer with a compressive modulus of 68 kPa (FIG. 17). The modulus then increased with increasing concentrations of the polymer to reach 4955 kPa at 10% w/w polymer. In contrast, alginates oxidized with 50 and 25 equivalents of periodate formed gels starting at 5% and 6% w/w polymer respectively with a compressive modulus of 11 and 168 kPa (FIG. 17). The maximum compressive modulus attained was 3517 and 1485 kPa, respectively. This trend is expected in these hydrogels as alginates oxidized to a lower level contain fewer reactive aldehydic groups and, hence, form a lower number of cross-links in comparison to higher oxidized alginates. This decrease in the intramolecular cross-link density likely results in hydrogels with low mechanical strengths.

Example 22

Hydrogels were formed at various concentrations of adipic dihydrazide. Highly oxidized alginates (100% theoretical) formed hydrogels with a compressive modulus of 560 kPa at 50 mM adipic dihydrazide. The compressive modulus then increased with increasing concentrations of adipic dihydrazide to reach a maximum of 4000 kPa at 200 mM adipic dihydrazide (FIG. 18). Above this concentration, the compressive modulus decreased. This suggest that intermolecular cross-linking competes with intramolecular cross-linking above 200 mM of adipic dihydrazide. This would result in weaker gels and would explain the decrease in the compressive modulus. Alginate that is oxidized with 50% periodate equivalents formed hydrogels with a maximum compressive modulus of 1135 kPa at 150 mM adipic dihydrazide (FIG. 18). Again, the modulus decreased as the concentration of adipic dihydrazide was increased further. Alginates that were oxidized with 25% periodate formed weak inhomogeneous gels. The compressive modulus of these gels was low and had large standard deviations. At this low aldehyde concentration the cross-link density is obviously very low.

Example 23

To determine the contribution to hydrogelling of ionic cross-linking from divalent cations, particularly calcium, in oxidized alginate hydrogels, gels were formed with a constant concentration of covalent cross-links and the concentration of calcium ions was varied. Sodium alginate oxidized with 100% periodate equivalents formed hydrogels with higher compressive modulus as the calcium concentration was increased to reach a maximum modulus of 4500 kPa at 40 mM calcium chloride (FIG. 19). Above this concentration the gels were inhomogeneous and exhibited variable strengths. This could be the attributed to the rapid kinetics of the ionic cross-links in comparison to the slow covalent cross-link. At high calcium concentrations, ionic cross-linking increases the rate of gelling, and thus results in higher intermolecular cross-links. The same trend was observed with lower oxidized alginates (50% periodate), where the maximum compressive modulus attained was at 60 mM calcium chloride (FIG. 19). Above this concentration hydrogels with low compressive moduli were formed. The maximum compressive modulus for alginate that is oxidized with 100% equivalents of periodate was at 40 mM calcium ions whereas the maximum was at 60 mM for alginate oxidized with 50% periodate (FIG. 19). The lower the degree of oxidation of alginate, the higher the number of intact guluronate units in the polymer. This results in an increase in the number of potential ionic cross-linking sites in the hydrogels.

Example 24

Introducing covalent cross-links in addition to ionic cross-links with divalent cations improve the physical properties of alginate hydrogels (Bouhadir et al., Synthesis of cross-linked poly(aldehyde guluronate) hydrogels. Polymer 1999; 40: 3575–3584; Eiselt et al., Rigidity of two-component hydrogels prepared from alginate and poly(ethylene glycol)-diamines. Macromolecules 1999; 32: 5561–5566); Rowley et al., Synthesis and Characterization of Covalently Crosslinked Alginates. (submitted). Reactive aldehyde groups in oxidized alginate were used to cross-link these polymers, in contrast to previous approaches where alginate was oxidized with sodium periodate and cross-linked with polyethyleneimine via the formation of schiff's bases (Birnbaum et al., Covalent stabilization of alginate gels for the entrapment of living cells. Biotech. Lett. 1982; 3: 393–400). Schiff's bases are relatively unstable in aqueous solutions and, therefore, it is advantageous to cross-link oxidized alginates with a functional group that is more reactive than amines. One such group is the hydrazide group used here that reacts with the pendant aldehyde group in the polymer to form a hydrazone bond, as described above.

Uncrosslinked alginate hydrogels degrade in an uncontrollable manner following the release of calcium ions into the surrounding medium (Shoichet et al., Stability of hydrogels used in cell encapsulation: An in vivo comparison of alginate and agarose. Biotechnol Bioeng 1996; 50: 374–381). To evaluate whether the degradation of cross-linked oxidized alginates can be controlled, gels were formed with 10% w/w oxidized alginates (oxidized with 100 equivalents of periodate) and cross-linked with adipic dihydrazide and/or calcium. The percentage weight loss of these gels was then calculated (FIG. 20). Hydrogels formed at 100 mM adipic dihydrazide degraded after 3 weeks of incubation at a rate of 5% per day. Hydrogels cross-linked at 150 mM adipic dihydrazide and 40 mM calcium chloride degraded at a lower rate of 2.5% per day (FIG. 20). Only 40% of the gel weight dissolved after 15 weeks. Therefore, hydrogels can be formed with this approach that degrade in time frames from three weeks to more than four months by simply varying the number of covalent and ionic cross-links.

Materials and Methods for Examples 19–24

Materials. Sodium alginate was purchased from Pronova Biomaterials (Drammen, Norway). Sodium periodate, ethylene glycol, sodium cyanoborohydride, and anhydrous KBr were purchased from the Aldrich Chemical Company (Milwaukee, Wis.) and used as received. Ethanol (95%) and concentrated hydrochloric acid were purchased from Fisher Scientific Company (Fair Lawn, N.J.) and were used as received. Infrared spectra were recorded as % transmittance using a Nicolet 5DX FTIR spectrophotometer and a Hewlett Packard 7470A plotter. Samples were pressed as KBr pellets using a hydraulic press (Carver, Inc.).

Size Exclusion Chromatography (SEC). SEC analysis was performed on a liquid chromatograph consisting of a SpectraSystem P1000 pump (Thermal Separation Products), a Rheodyne 7010 manual injector, a dual differential viscometer and right angle laser light scattering (RALLS) detector (Viscotek T 60, $\lambda=670$ nm) and a laser refractometer detector (Viscotek LR40, $\lambda=670$ nm), the detectors being connected in parallel. The mobile phase consisted of aqueous sodium nitrate (0.1 M) and was periodically degassed with an on-line degasser. The mobile phase was delivered at ambient temperature with a nominal flow rate of 0.7 ml/min. The separations were carried out on two TSK GMPW$_{XL}$ (TosoHaas, 7.8×300 mm) mix bed columns. Polymers were dissolved in mobile phase solvent at a concentration of 1–3 mg/ml by mechanical stirring for a minimum of 6 hrs until completely hydrated. A 100 µl injection volume was used for all analyses. The chromatograms were analyzed using the TriSEC 3.0 GPC software (Viscotek). A differential index of refraction (dn/dc) of 0.154 ml/g was used.

Mechanical analysis. The mechanical properties of cross-linked PAG gels were determined using a MTS Bionix 100 mechanical tester (MTS Systems Corporation, France). Samples were compressed with a load cell at room temperature with a constant deformation rate of 1.00 mm min$^{-1}$. The diameter of the indentor was 3.15 mm. These samples were measured for each condition in quadruplicate, and the values given in the figures represent the mean and the standard deviation.

Oxidation of sodium alginate. A 1 L Erlenmeyer flask was wrapped with aluminum foil and charged with sodium alginate (8.0 g). Double distilled water (800 ml) was added and the mixture was stirred until the solid dissolved. An aqueous solution of sodium periodate (0.25 M, 162 ml) was added and the reaction was stirred for 24 h at room temperature. Ethylene glycol (2.3 ml) was then added to the reaction mixture to reduce any unreacted periodate. The reaction was stirred for 0.5 hr at ambient temperature and the solution was filtered and exhaustively dialyzed (Spectra/Pro membrane, MWCO 3500) against double distilled water for three days. The water was changed at least three times a day. The solutions were then concentrated to around 100 ml, and freeze dried under reduced pressure to yield a white product (6.9 g, 86%). IR (KBr pellet, cm$^{-1}$) 3336, 2942, 1730, 1622, 1406, 1321, 1159, 1117, 1026.

Determination of the degree of oxidation. The degree of oxidation of alginate was determined by measuring the percentage of periodate that was consumed before quenching with ethylene glycol. The periodate consumption was monitored spectrophotometrically using theodene. Briefly, equal volumes of freshly prepared aqueous solutions of potassium iodide (20% w/v in pH 7.0 sodium phosphate buffer) and thyodene solution (10% w/v in pH 7.0 sodium phosphate buffer) were mixed as an indicator solution. A 100 ml Erlenrneyer flask was covered with aluminum foil and charged with an aqueous solutions of alginate (50 ml, 1.0% w/v) and an aqueous solution of sodium periodate (10.1 ml, 0.25 M). The mixture was stirred at room temperature. At different time intervals, aliquots (0.3 ml) were rapidly removed and diluted to a volume of 100 ml using DI H$_2$O. A 0.5 ml aliquot of this solution was immediately mixed with 1.0 ml of the indicator solution in a cuvet. The concentration of the unreacted periodate was measured spectrophotometrically at 486 nm. This number was then subtracted from the original concentration of periodate to yield the amount of periodate that was consumed.

Representative procedure for cross-linking oxidized alginate. In 24-well plates, solutions of 50 µl, 100 µl, 150 µl, 200 µl, and 250 µl aqueous oxidized alginate (20% w/w) were pipetted in four wells each. Aqueous adipic dihydrazide (150 µl, 0.5 M) was then added to each well and the final volume was adjusted to 0.5 ml with dd. H$_2$O. The contents of each well were mixed and allowed to gel for one hour at ambient temperature on a mechanical shaker. The thickness of each gel was then measured using a micrometer gauge and the compressive modulus was determined with a mechanical tester. Afterwards, the compressive moduli from each condition (four samples) were averaged and plotted against the weight percentage of oxidized alginate in each gel. IR (KBr pellet, cm$^{-1}$) 3554, 3472, 3414, 3236, 1660, 1622, 1406, 1154, 1095, 1036.

Determination of the swelling ratio of the hydrogels. Hydrogels were formed at various concentrations of oxidized alginate, adipic dihydrazide and calcium chloride in 24-well plates. The hydrogels were immersed in deionized water and incubated at 37° C. for 24 hr to reach the equilibrium swelling. The hydrogels were transferred to 2 ml vials and weighed (wet weight). The gels were then frozen, lyophilized and the dried samples were weighed (dry weight). The swelling ratio was defined as the ratio of (wet weight−dry weight)/(dry weight).

Hydrogel degradation. The degradation study was performed with alginate that was oxidized using 100 equivalents of sodium periodate. Aqueous solutions of oxidized alginate (125 µl, 20% w/w) and adipic dihydrazide (125 µl, 0.5 M) with calcium chloride (80 mM) were mixed in 15 ml conical tubes (in quadruplicates), and allowed to gel for 5 hours. Solutions of Dulbecco's Modified Eagles Medium (DMEM, 10 ml) were added and the tubes were incubated at 37° C. The medium was replaced with fresh medium on a weekly basis. Four tubes were removed every week and the medium was decanted. The gels were frozen and lyophilized, and the dry solid was weighed.

Example 25

Commercially available high molecular weight alginate was hydrolyzed under acidic conditions to break down the β-glycosidic linkages between the mannuronate and guluronate residues as in Example 1. Polyguluronate was then isolated by precipitation at pH 2.85, and its molecular weight was 6200 daltons as determined by size exclusion chromatography. Polyguluronate was then oxidized with sodium periodate to yield the poly(aldehyde guluronate), PAG. The degree of oxidation was controlled by the mole equivalent of sodium periodate used in each reaction. The degree of oxidation of PAG used in this study was 87±1%. PAG was subsequently cross-linked with a bi-functional cross-linker, adipic dihydrazide, to form hydrogels, as described in Example 1. A high efficiency of this coupling was confirmed using FT-IR spectra and quantification of the cross-link density. The degree of swelling of PAG hydrogels was analyzed after the hydrogels had reached the equilibration swelling in aqueous DMEM. The swelling ratio ranged from 8 to 10 for hydrogels made with varying extents of cross-linking (Table 4):

TABLE 4

| PAG (% w/w) | Adipic dihydrazide (mM) | CaCl$_2$ (mM) | Swelling ratio |
| --- | --- | --- | --- |
| 6.0 | 100 | 40 | 10.9 ± 0.2 |
| 6.0 | 150 | 40 | 8.6 ± 0.1 |
| 6.0 | 200 | 40 | 8.4 ± 0.1 |
| 6.0 | 250 | 40 | 8.2 ± 0.1 |
| 6.0 | 150 | 0 | 10.3 ± 0.1 |
| 7.0 | 150 | 0 | 9.8 ± 0.1 |
| 8.0 | 150 | 0 | 9.5 ± 0.2 |

The swelling was minimally affected by alterations in the cross-linking densities used in this study. This finding may be attributed to the low molecular weight of the poly (aldehyde guluronate) chains utilized to form these hydrogels.

Example 26

The reaction described in Example 2 was utilized to incorporate daunomycin into hydrogels for localized drug delivery. HPLC was used to determine the amount of daunomycin that reacted with adipic dihydrazide before the addition of PAG. Mixtures of daunomycin and adipic dihydrazide were analyzed and found to contain 88.5% of the daunomycin-adipic dihydrazide conjugate and 11.5% of free drug (FIG. 21). The amount of daunomycin that was covalently incorporated into the hydrogel was next determined by quantifying the amount of free drug in the hydrogel. Hydrogels containing daunomycin or trypan blue were synthesized, frozen, lyophilized, and crushed to form powders. The free drug was then dissolved in water and the resulting mixture was filtered to remove any fine particles. The concentration of the free drug was then determined spectrophotometrically. Trypan blue was used as a control since it does not contain aldehyde or ketone groups for coupling to PAG and has a comparable molecular weight to daunomycin. Only two percent of the trypan blue was retained in the hydrogel. In comparison, 86.9±0.1% of daunomycin remained in the gelatinous particles. Moreover, hydrogels containing trypan blue that were incubated in DMEM released the entire drug within 24 hours. These findings clearly indicate that daunomycin is covalently coupled to the hydrogel through the adipic dihydrazide molecule. The daunomycin incorporation in the hydrogels correlates well with the percentage of daunomycin-adipic dihydrazide conjugate that was determined by HPLC analysis.

Example 27

The release of the free drug from the hydrogel will be controlled by the chemical hydrolysis of the hydrazone bond between the drug and the adipic dihydrazide spacer, followed by the diffusion of the drug from the hydrogel. However, the hydrolysis of the linkage between adipic dihydrazide and PAG could also release the daunomycin-adipic dihydrazide conjugate. In this case, an inactive form of the drug would be released (prodrug), which would be later activated by the hydrolysis of the linkage between adipic dihydrazide and daunomycin. To determine the percentage of free drug that is released, samples were periodically analyzed by HPLC. Uncoupled free daunomycin was quantitatively released from cross-linked PAG hydrogels at all times (FIG. 21c).

Example 28

The extracellular pH of most tumors is slightly lower than that of normal tissues (Tannock et al., Acid pH in tumors and its potential for therapeutic exploitation. Cancer Res. 1989, 49, 4373–4384; and Gerweck et al., Cellular pH gradient in tumor versus normal tissue: potential exploitation for the treatment of cancer. Cancer Res. 1996, 56, 1194–1198) and this could affect the release kinetics of drugs from PAG hydrogels. To investigate the possible role of pH on drug release, the release of daunomycin from 6% w/w PAG hydrogels at 150 mM adipic dihydrazide was monitored at different pH conditions (FIG. 22). Daunomycin was released at a rate of 1% per day from hydrogels incubated at neutral condition, but daunomycin was released at a significantly higher rate (1.8% per day) from hydrogels incubated in acidic medium. This result is likely caused by the higher rate of hydrolysis of hydrazone bonds under acidic conditions (Greenfield et al., Evaluation in vitro of adriamycin immunoconjugates synthesized using an acid-sensitive hydrazone link. Cancer Res. 1990, 50, 6600–6607).

Example 29

The antitumor activity of the daunomycin released from PAG hydrogels was evaluated in vitro using a standard cytotoxicity assay with KB cells (Prichard et al., Three-dimensional analysis of the synergistic cytotoxicity of ganciclovir and zidovudine. Antimicrob. Agents Chemother. 1991, 35, 1060–1065.) The media collected from control hydrogels had no effect on cell growth. The $IC_{50}$ of the daunomycin-adipic dihydrazide conjugate (in the presence of 100-fold excess of adipic dihydrazide) was 0.224±0.091 µM compared to 0.202±0.048 µM for the free daunomycin (Table 5):

TABLE 5

| Sample | $IC_{50}$ (µM) |
| --- | --- |
| Free daunomycin | 0.202 ± 0.048 |
| Daunomycin-adipic dihydrazide | 0.224 ± 0.091 |
| Released daunomycin after 1 week | 0.560 ± 0.149 |
| Released daunomycin after 2 weeks | 0.349 ± 0.176 |
| Released daunomycin after 3 weeks | 0.805 ± 0.229 |

The activity of the released daunomycin slightly decreased during the first 3 weeks, suggesting that the released drug might be partially degraded. The glycosidic linkage between the daunosamine and daunomycinone units of the drug has been previously reported to undergo hydrolytic cleavage under neutral to basic conditions (Pujol et al., Stability study of epirubicin in NaCl 0.9% injection. Ann. Pharmacother. 1997, 31, 992–995; Nyhammar et al., Stability of doxorubicin hydrochloride and vincristine sulfate in two portable infusion-pump reservoirs, Am. J. Health-System. Pharm. 1996, 53, 1171–1173). The activity of daunomycin released in spent media did not differ significantly from that released in fresh media. PAG and adipic dihydrazide were also tested to ensure that the noted cytotoxicity was not caused by these components of the hydrogels. Neither aqueous PAG nor adipic dihydrazide had a significant effect on the growth of KB cells over the range of concentrations tested.

Materials and Methods for Examples 25–29

Materials. Sodium alginate was purchased from Pronova Biomaterials (Drammen, Norway). Sodium periodate, adipic dihydrazide, ethylene glycol, and calcium chloride were purchased from Aldrich Chemical Company (Milwaukee, Wis.) and were used as received. Daunomycin hydrochloride was purchased from Fluka Chemical Corporation (Ronkonkoma, N.Y.). Dulbecco's Modified Eagle's Medium (DMEM) was purchased from Life Technologies (Grand Island, N.Y.). KB cells (an established line of human epidermoid carcinoma cells) were a gift from Dr. John Drach (Department of Biologic & Materials Sciences, University of Michigan).

Instruments. UV/VIS spectra were collected on a Perkin Elmer Lambda 12 UV/VIS spectrophotometer. High performance liquid chromatography (HPLC) analysis was performed using a Hewlett Packard Series II 1090 Liquid Chromatograph with a photodiode array detector and a Phenomenex Hypersil C18 column. The mobile phase consisted of water and acetonitrile ($H_2O/CH_3CN$=82/18, v/v) and the aqueous component contained 0.025% acetic acid. The system was programmed for gradient elution starting with 82/18 ($H_2O/CH_3CN$, v/v) for 2 min then raised to 50/50 during 4 min then back to 82/18. The elution of the drug was monitored at 480 nm.

Synthesis of the poly(aldehyde guluronate), PAG. PAG was synthesized according to a previously reported procedure (Bouhadir et al., Synthesis of cross-linked poly(aldehyde guluronate) hydrogels. Polymer 1999, 40, 3575–3584). Briefly, sodium alginate was hydrolyzed under acidic conditions and the polyguluronate fragments were isolated. Polyguluronate was then oxidized with sodium periodate to yield PAG. The product was analyzed by $^1$H-NMR, FTIR, and the aldehyde content was quantified using trinitrobenzene sulfonic acid.

Preparation of cross-linked PAG hydrogels. Daunomycin (10 µl, 25 mg/ml solution in DMSO) was added to aqueous solutions of adipic dihydrazide (25 to 125 µl, 0.5 M) in 5 ml sterile tubes. After 10 min, aqueous solutions of PAG (150–200 µl, 20% w/w) were added and the total volume was diluted to 250 µl with Dulbecco's Modified Eagle's Medium (DMEM, pH 7.4) containing penicillin and streptomycin (100 units/ml and 100 µg/ml, respectively). The mixtures were mixed and allowed to stand at room temperature for 1 hr to form hydrogels. In the result section of this manuscript, hydrogels are described by their final PAG concentrations (% w/w) and final adipic dihydrazide concentrations (mM).

Determination of the swelling ratio of the hydrogels. Hydrogels were formed at various concentrations of PAG, adipic dihydrazide and calcium chloride in 24-well plates. The hydrogels were immersed in DMEM (pH 7.4) and incubated at 37° C. for 24 hr to reach the equilibrium swelling. The hydrogels were transferred to 2 ml vials and weighed (wet weight). The gels were then frozen, lyophilized and the dried samples were weighed (dry weight). The swelling ratio was defined as the ratio of (wet weight–dry weight)/(dry weight).

Determination of the incorporated daunomycin. To quantify the amount of daunomycin that is incorporated in the gels, two sets of hydrogels were formed as described above. One set was loaded with daunomycin (0.20 mg, 0.355 µmol) and the other with trypan blue (0.32 mg, 0.333 µmol). After gelation, the hydrogels were frozen and lyophilized. The dried solid in each tube was crushed and 2 ml of double distilled water was added. The solutions were then sonicated for 30 minutes, quantitatively transferred to 5 ml volumetric flasks, and diluted with double distilled water. Each solution was filtered through a 0.22 µm filter and the concentration of the dissolved drug was quantified spectrophotometrically at 480 nm for daunomycin and 588 nm for trypan blue.

In vitro release of daunomycin in fresh medium. Hydrogels were formed in 15 ml sterile tubes as described above. Aqueous solutions of 5 ml of DMEM containing penicillin and streptomycin were added to each gel. The hydrogels were then incubated at 37° C. and the medium was replaced with fresh DMEM (5 ml) periodically. The concentration of the released drug in the medium was quantified spectrophotometrically at 480 nm.

In vitro release of daunomycin in spent medium. Spent media was obtained from cultured KB cells. Approximately $2\times10^4$ cells were seeded in a 162 cm² flasks containing 50 ml media and incubated at 37° C. for 3 to 4 days until cells had approximately reached confluency. The pH of the collected media was not significantly different from fresh media (pH 7.4). Hydrogels containing daunomycin (10 µl, 25 mg/ml in DMSO) were formed at 6% w/w PAG and 150 mM adipic dihydrazide. The hydrogels were exposed to 2.5 ml of spent Minimal Essential Media with Hanks' salts (MEMH) without phenol red that contained 10% calf serum and penicillin/streptomycin (100 units/ml and 100 µg/ml, respectively). The medium was replaced weekly and the concentration of daunomycin that was released from the hydrogels in spent media was determined at 480 nm.

Cytotoxicity assay with KB cells. The inhibitory concentrations of the released daunomycin that killed 50% of the cells ($IC_{50}$) were determined using an established cytotoxicity assay with KB cells as described previously (Prichard et al., Three-dimensional analysis of the synergistic cytotoxicity of ganciclovir and zidovudine. Antimicrob. Agents Chemother. 1991, 35, 1060–1065). Hydrogels at a final concentration of 6% w/w PAG and 150 mM adipic dihydrazide containing 250 µg of daunomycin were prepared and incubated in 5 ml sterile media at 37° C. The media was tested and replaced with fresh media (5 ml) periodically. As a control, a set of hydrogels were not loaded with the drug and treated in the same fashion as above. KB cells were cultured and seeded at a density of $5\times10^3$ cells/well in 96-well plates with a total volume of tissue culture medium of 200 µl/well. Cells were allowed to attach for 1 day before adding drug solutions or aliquots from the collected samples. Eight dilutions were used for each sample (each being one-third the concentration of the previous dilution). After 48 hr, cells were fixed with 95% ethanol for 5 min, rinsed with tap water, and stained with 2.5 mM crystal violet in 20% aqueous methanol for 5 min. The plates were rinsed again with tap water and 150 µl/well acidified ethanol (0.01 M HCl) was added to elute the dye from stained cells. The concentration of the dye in each well was measured spectrophotometrically at 570 nm. Dose-response curves were generated by plotting percent inhibition ([sample absorbency/control absorbency]×100) versus the log of the daunomycin concentration and fit to a line. $IC_{50}$ values were calculated using the equations for the best linear fit. $IC_{50}$ values of daunomycin released from the hydrogels exposed to both fresh and spent media were compared with those of daunomycin stored in DMSO or daunomycin conjugated with adipic dihydrazide for 15 min. before adding to the cells. Solutions containing only PAG, adipic dihydrazide, or material released from the hydrogels without daunomycin were also tested.

Example 30

For the water-soluble polymeric drug carriers aspect of the invention economical poly hydrazides can be synthesized from low molecular weight polyacrylamides, as shown in Equation 12:

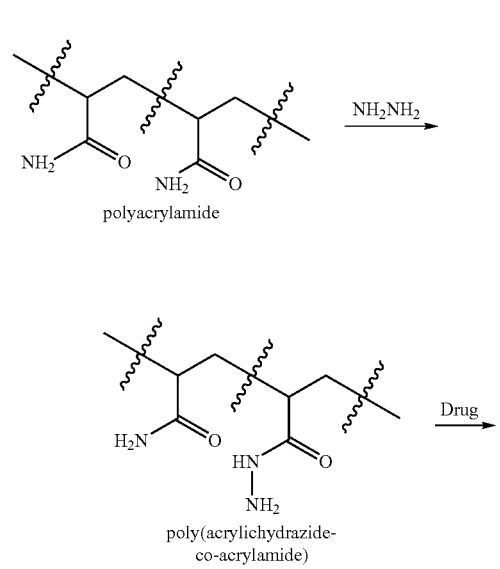

-continued

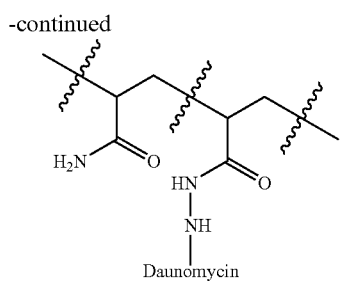

Hydrazinolysis of aqueous 50% w/w polyacrylamide in water (molecular weight average=10,000, 50 ml) by refluxing for three hours with aqueous hydrazine (35% w/w, 100 ml) yielded the poly(acrylic hydrazide-co-acrylamide) in quantitative yield. The product was precipitated by the addition of an equal volume of ethanol. The product was dried under reduced pressure. The solid was re-dissolved in water and dialyzed extensively until the dialysate gave a negative TNBS test. The solution was frozen and lyophilized to yield a white powder. TNBS analysis of the product indicated that 52% of the amide groups of polyacrylamide were transformed to hydrazide groups. The degree of substitution of amide groups can be controlled by varying the temperature, time, and equivalents of hydrazide used.

Example 31

Oxidized alginate undergoes hydrolytic cleavage in aqueous solutions to yield lower molecular weight oligomers. Alginate oxidized with 5% equivalents of sodium periodate was degraded over time in PBS buffer at physiological 37° C. These polymers started with an average molecular weights of 250 kDa and degraded over time to less than 28 kDa at physiological pH (7.4). At lower pHs (4.5) the degradation rate was slower and yielded 77 kDa oligomers. See FIG. 23. Thus, oxidized alginates with high molecular weights can be used to form hydrogels that degrade over time to release low molecular weight oligomers excretable from the body. The degradation of the oxidized alginates also depends on the temperature of the surrounding medium. For example, the degradation rate decreases as the temperature of the solution decreases; see FIG. 24. The average molecular weight of alginate oxidized with 5% equivalents of periodate reached 118 kDa at 4° C., and 58 kDa at room temperature (25° C.), compared to 26 kDa at 37° C. after 58 days of incubation. Alginates with low degree of oxidation do not form stable hydrogels with bifunctional cross-linkers such as adipic dihydrazide. However, they form relatively stable hydrogels when cross-linked with polyhydrazides such as poly(acrylichydrazide-co-acrylamide) via the formation of hydrazone bonds. After the hydrolysis of the hydrazone bonds, high molecular weight oxidized alginates are released and subsequently degraded to low molecular weight alginates that are excretable from the body.

Figure 1:
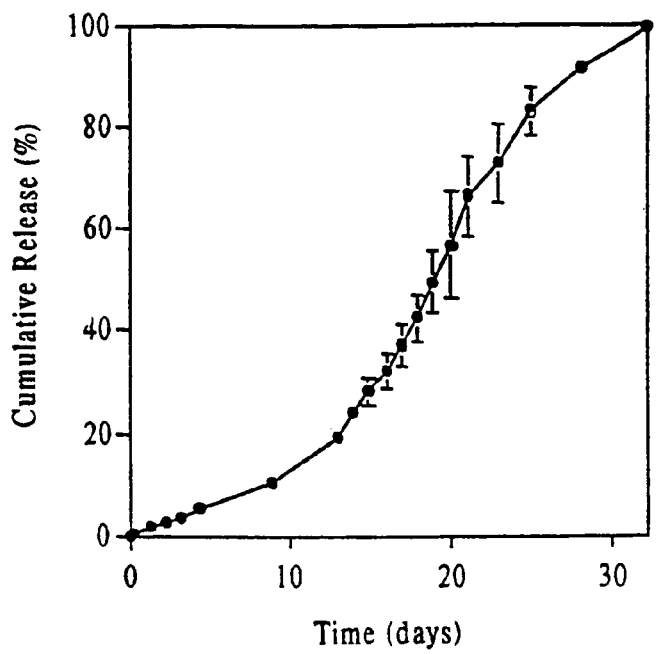
FIG. 1. A typical release profile of daunomycin from cross-linked PAG hydrogels.
Figure 2:
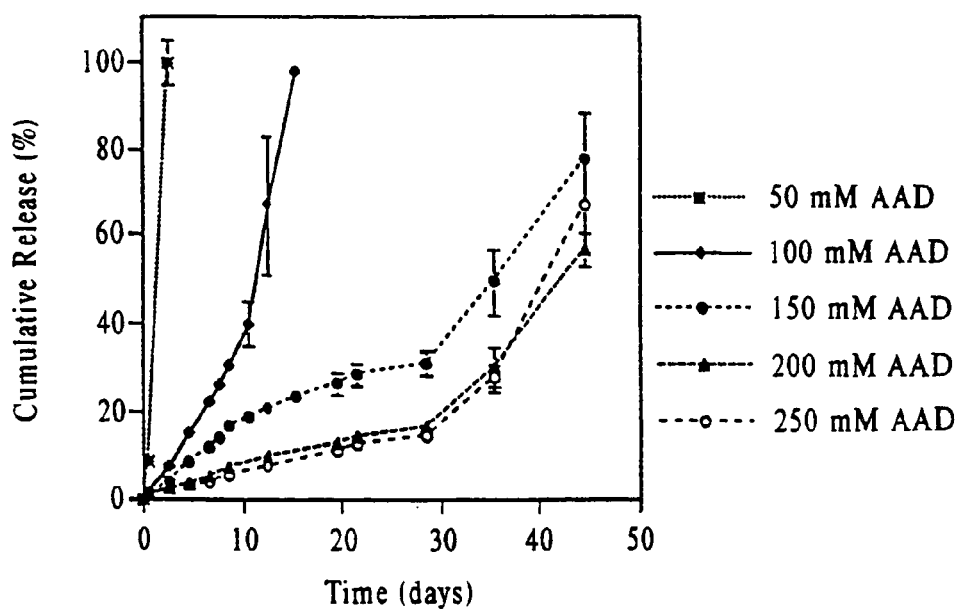
FIG. 2. The cumulative release of daunomycin over time from hydrogels cross-linked by 50 mM (*), 100 mM (♦), 150 mM (●), 200 mM (▲), and 250 mM (o) of adipic dihydrazide. All hydrogels were formed with 6% w/w PAG and 40 mM CaCl$_2$ and release was monitored following incubation in DMEM (pH 7.4) at 37° C.
Figure 3:
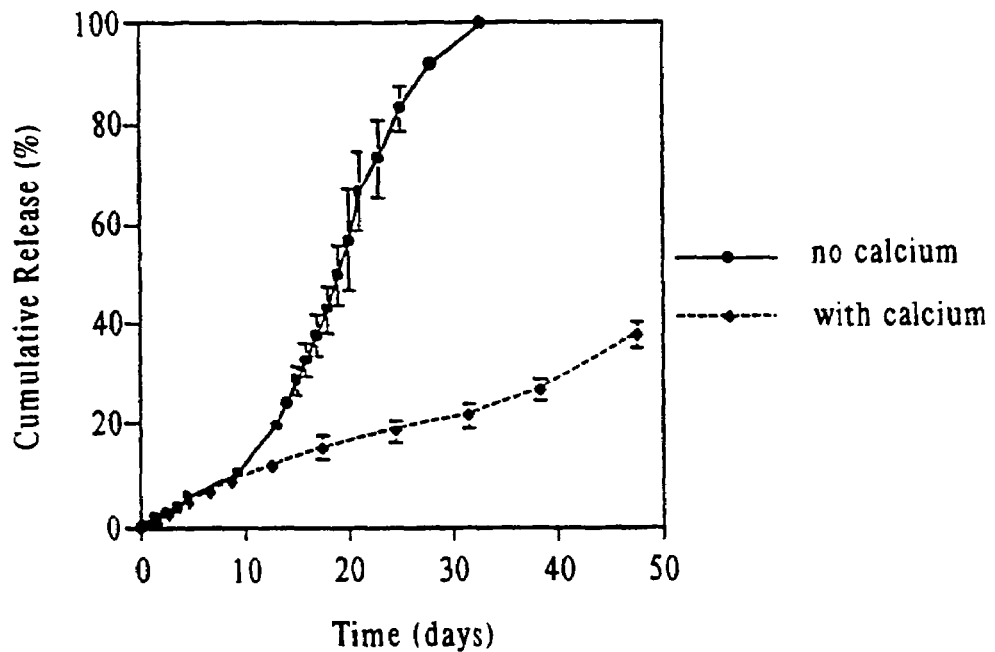
FIG. 3. The cumulative release of daunomycin over time from 6% w/w PAG hydrogels cross-linked by 150 mM AAD in the absence of calcium chloride (●) and in the presence of 40 mM calcium chloride (♦). Release was monitored following incubation in DMEM (pH 7.4) at 37° C.
Figure 4:
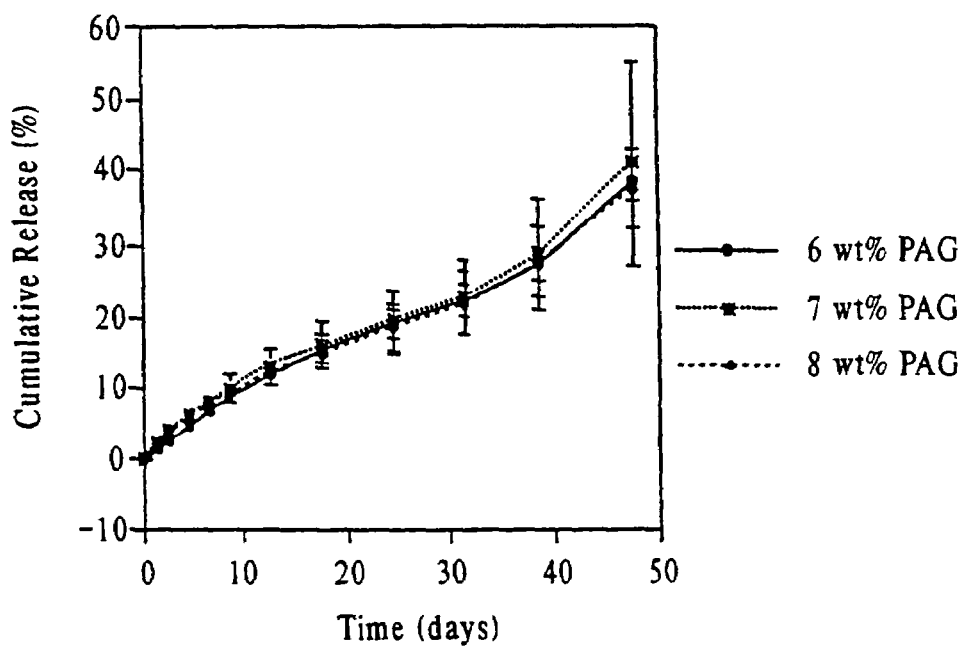
FIG. 4. The effect of the PAG concentrations on the release of daunomycin.
Figure 5:
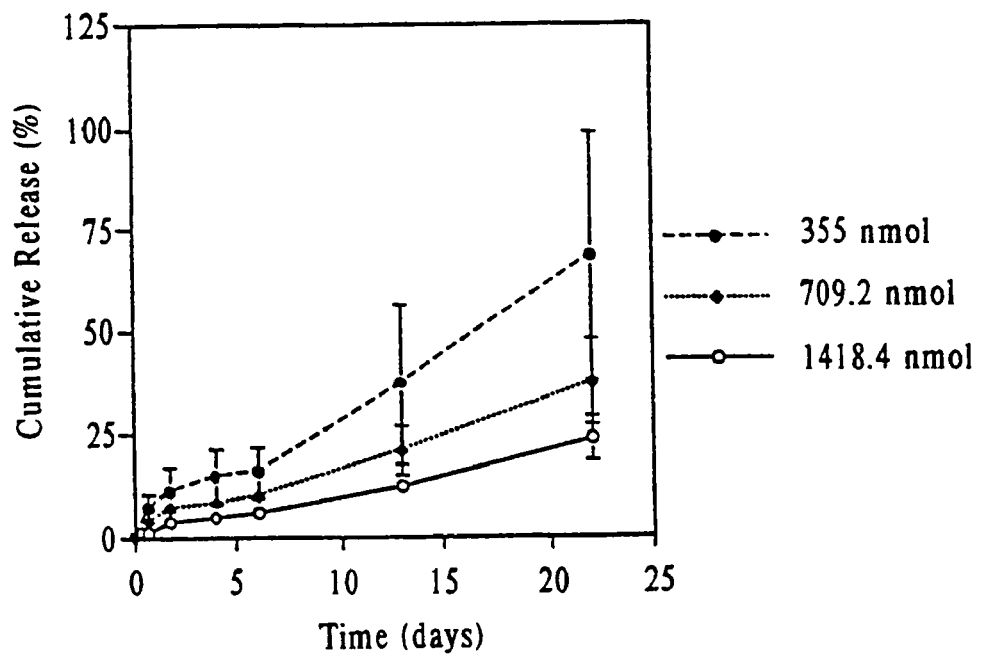
FIGS. 5 and 6. The release of daunomycin as a function of the concentration of loading of cross-linked daunomycin. As the concentration of daunomycin was increased, the percentage release of daunomycin decreased. No difference in the release profile was noted at different concentration of the drug.
Figure 6:
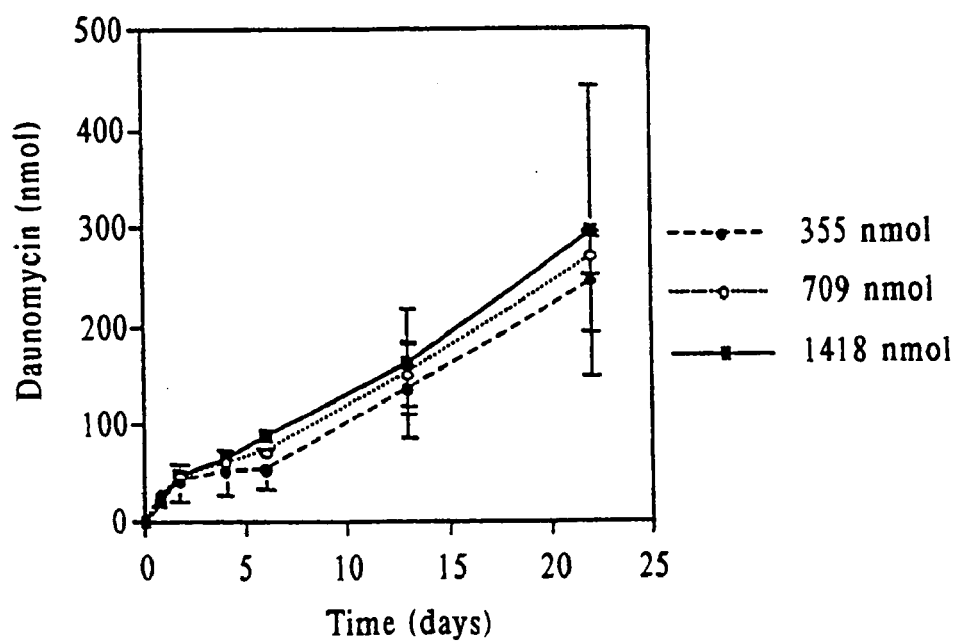
Figure 7:
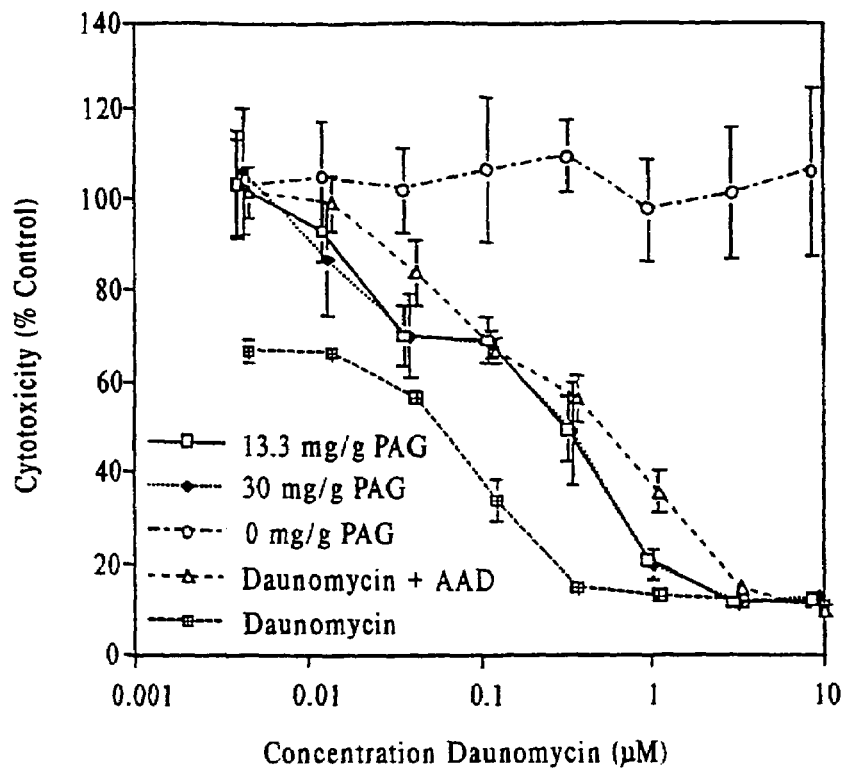
FIG. 7. The cytotoxicity of covalently bound daunomycin released from 6 wt % PAG gels containing either zero, 13.3 or 30 mg of drug per gram of PAG was compared with free drug and a daunomycin/AAD prodrug mixture.
Figure 8:
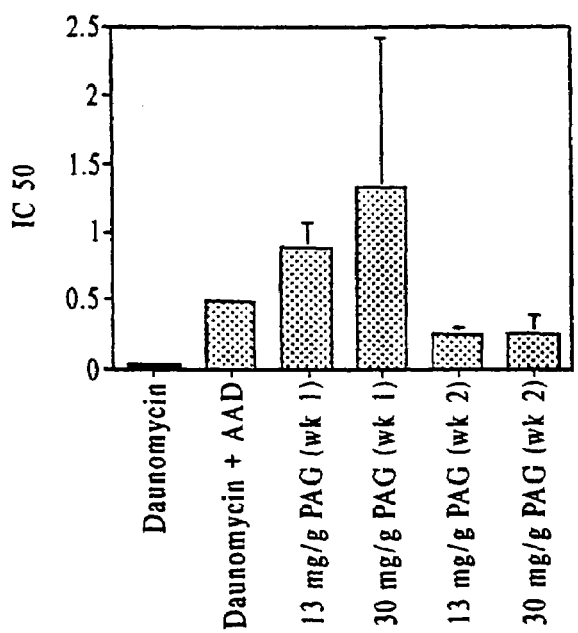
FIG. 8. IC 50 values for release of daunomycin during the second week of incubation.
Figure 9:
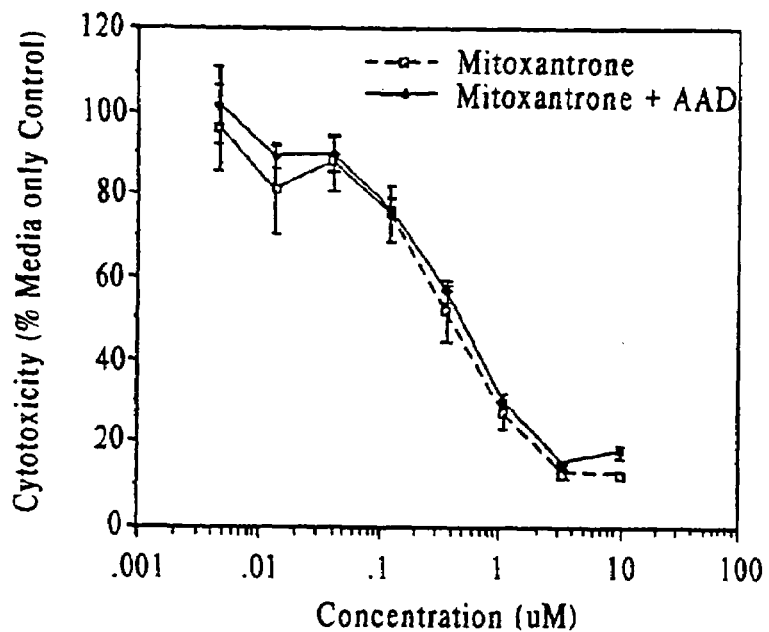
FIG. 9. The comparison of cytotoxicity for Mitoxantrone and Mitoxantrone with AAD shows that this anthracycline was not found to form a prodrug when mixed with AAD.
Figure 10:
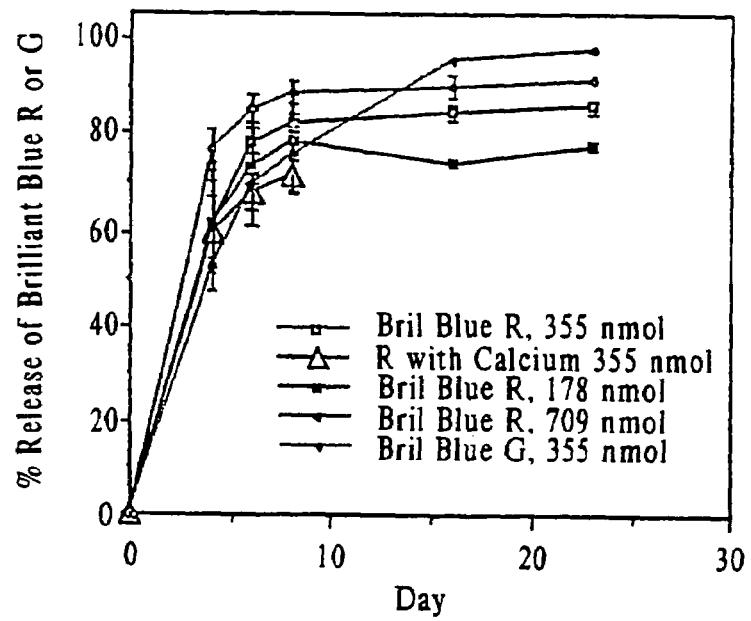
FIG. 10. Diffusion release of water soluble compounds was studied using the dyes Brilliant Blue R and G as models of compounds which have no functional group for covalent bonding.
Figure 11:
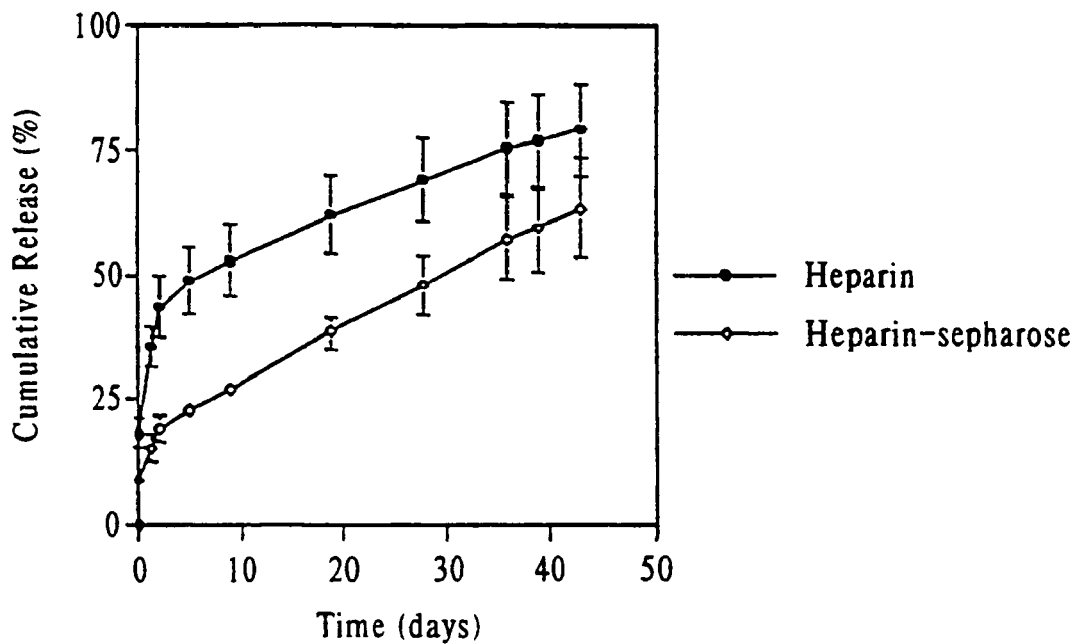
FIG. 11. A typical release profile of VEGF from cross-linked PAG hydrogels.
Figure 12:
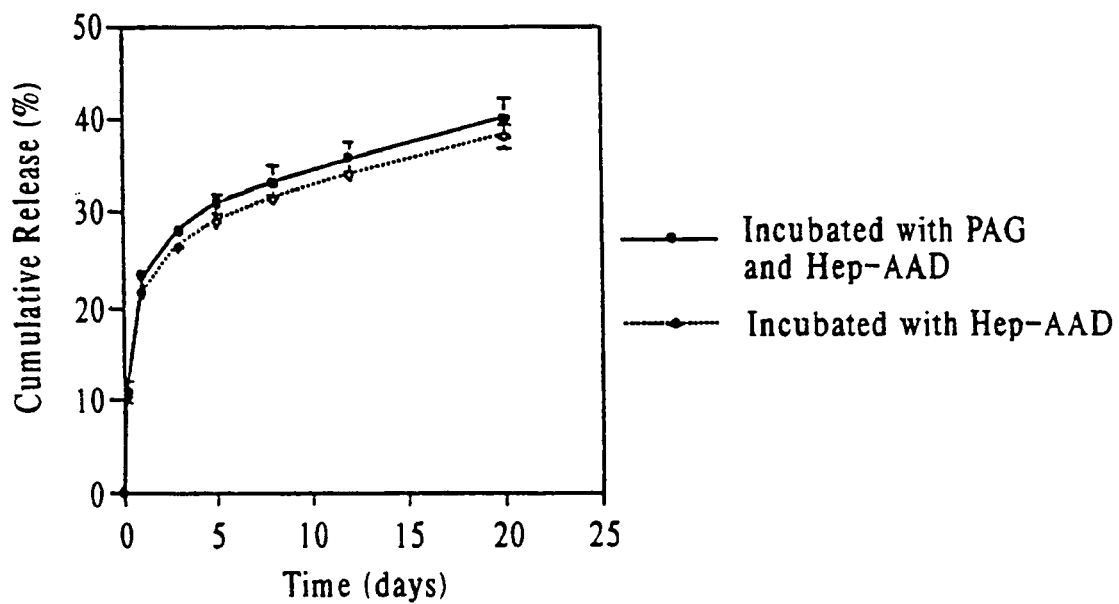
FIG. 12. The release of VEGF from PAG hydrogels.
Figure 13:
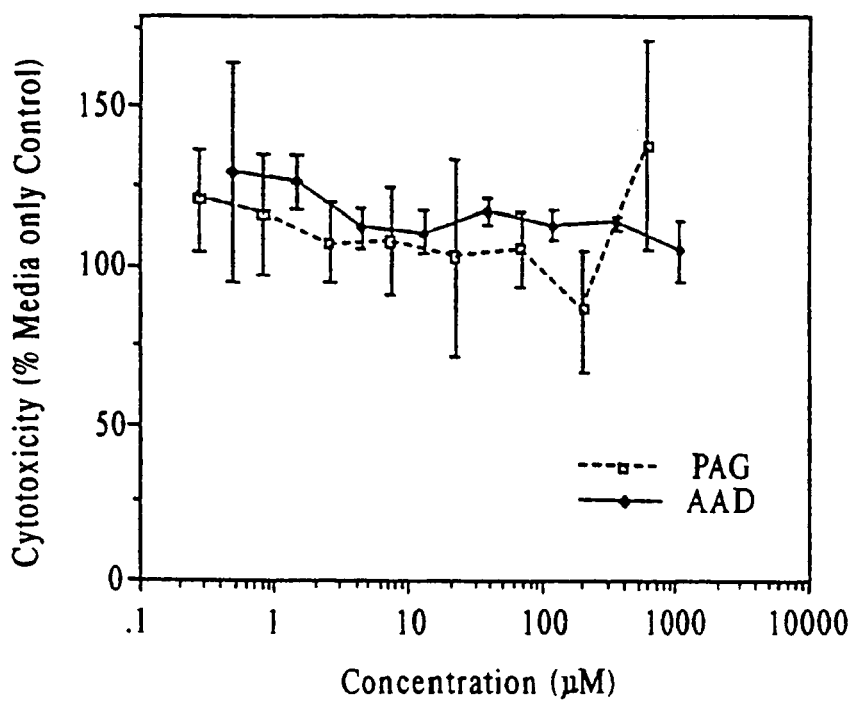
FIG. 13. In vitro tests using a standard cytotoxicity assay with KB cells showing compatibility of PAG and AAD.
Figure 14:
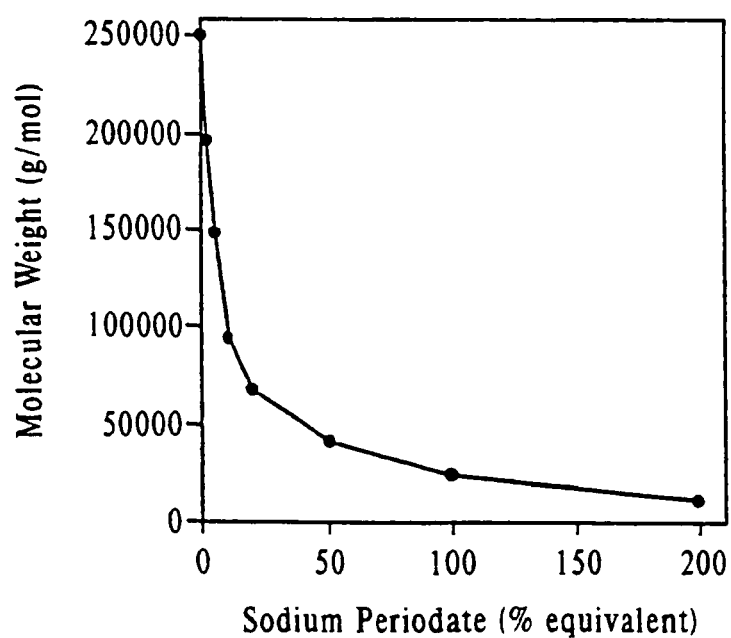
FIG. 14. Comparison of the molecular weights of partially oxidized alginates with increasing concentrations of sodium periodate in the oxidation reactions.
Figure 15:
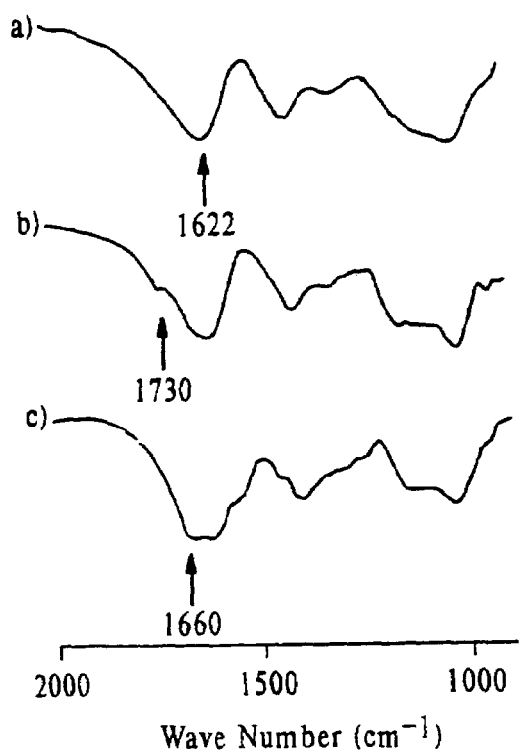
FIG. 15. FTIR spectra of (a) sodium alginate, (b) oxidized alginate (100% equivalents of periodate), and (c) cross-linked oxidized alginate.
Figure 16:
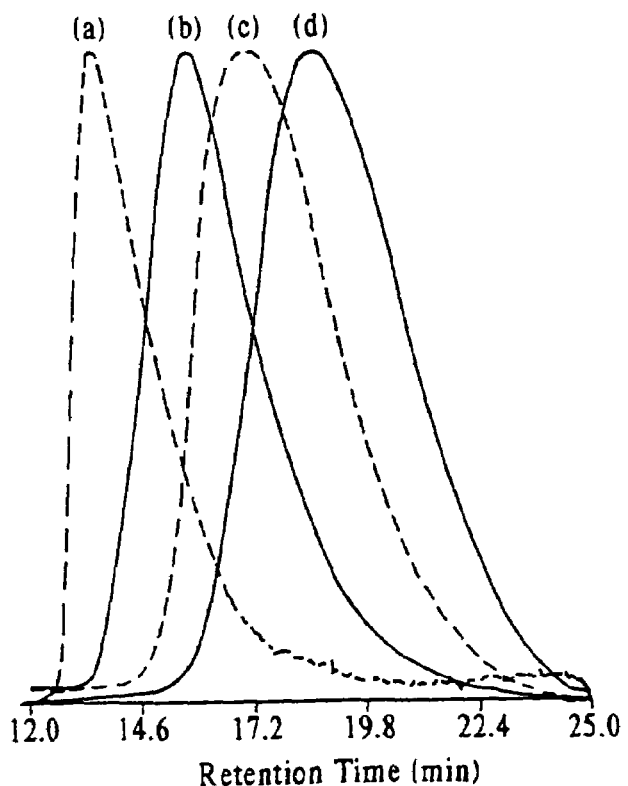
FIG. 16. Representative chromatograms of (a) sodium alginate, (b) 25%, (c) 50%, and (d) 100% oxidized alginate as detected by the differential refractive index detector. The solvent is comprised of 0.1M NaNO$_3$ (0.05% NaN$_3$) at a flow rate of 0.7 ml/min.
Figure 17:
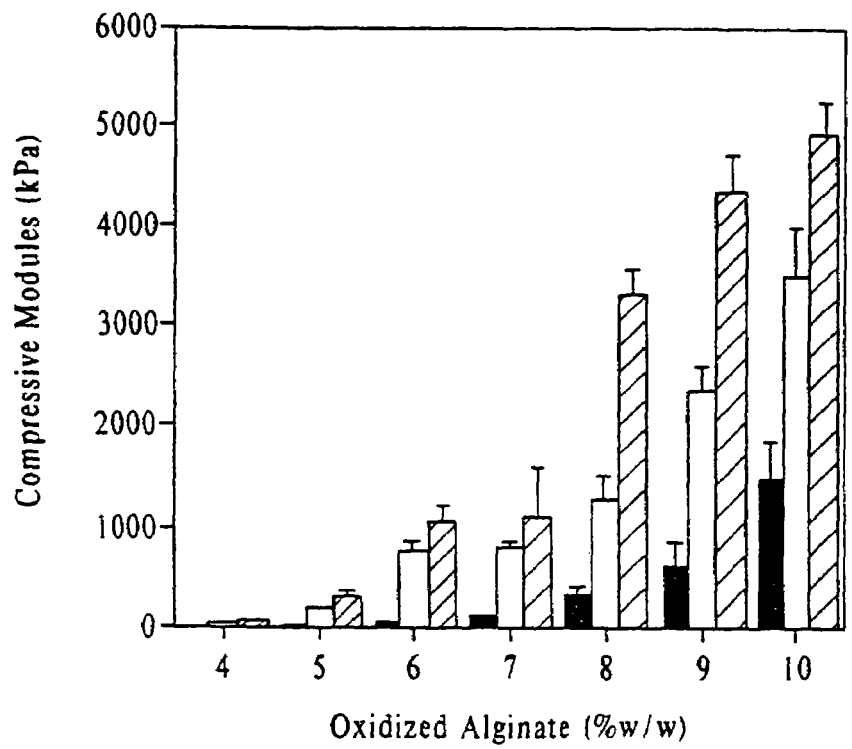
FIG. 17. The compressive modulus of cross-linked oxidized alginate hydrogels as a function of polymer concentration and degree of oxidation. The polymer was comprised of alginate oxidized with 25% (black), 50% (white), and 100% (striped) equivalents of sodium periodate. All hydrogels were cross-linked with adipic dihydrazide (150 mM) in dd water.
Figure 18:
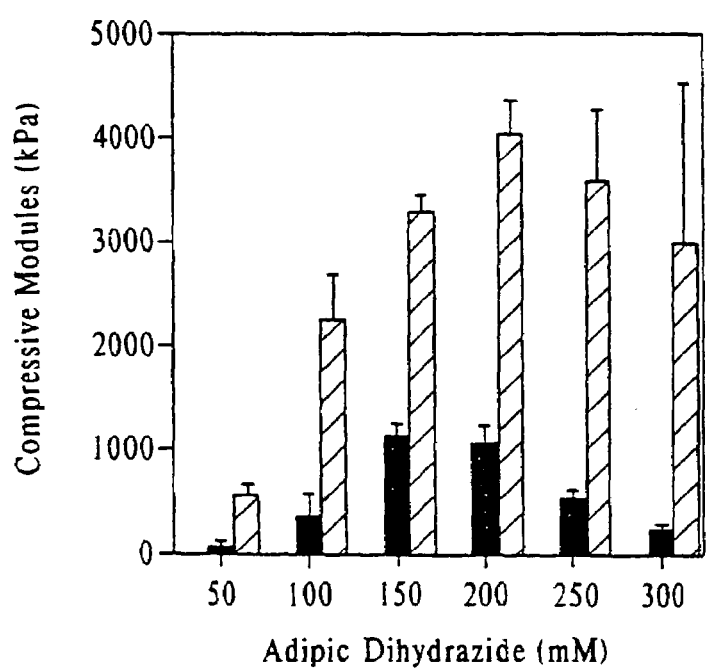
FIG. 18. The compressive modulus of cross-linked oxidized alginate hydrogels as a function of cross-linker concentration and alginate degree of oxidation. Alginate was oxidized with 50% (solid) and 100% (striped) equivalents of sodium periodate. All hydrogels were prepared with 6% w/w oxidized alginate and 40 mM calcium chloride in dd. water.
Figure 19:
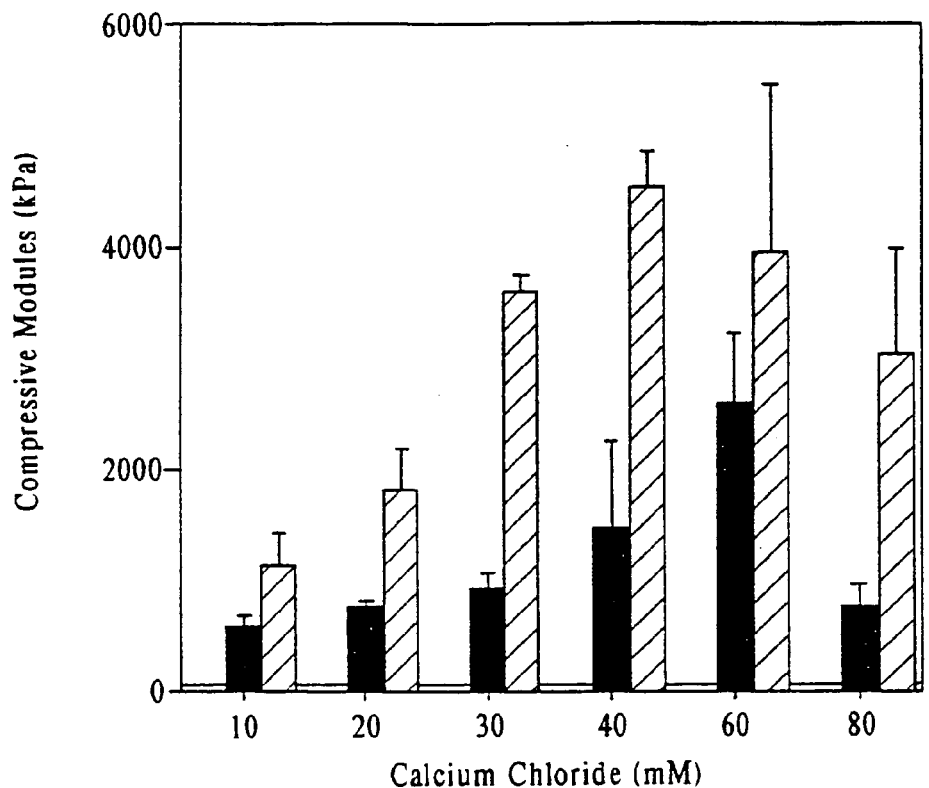
FIG. 19. The compressive modulus of cross-linked oxidized alginate hydrogels as a function of calcium ion concentration and alginate degree of oxidation. Alginate used was oxidized with 50% (black) and 100% (striped) sodium periodate. All hydrogels were prepared with 6% w/w oxidized alginate and 200 mM adipic dihydrazide in dd. water.
Figure 20:
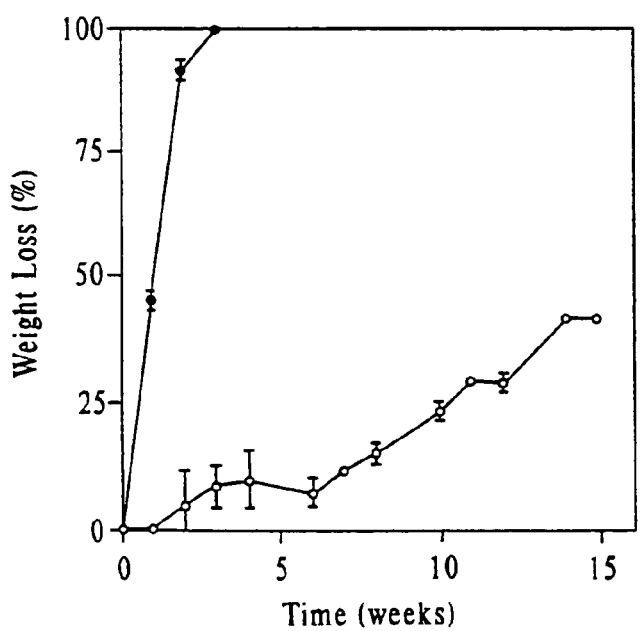
FIG. 20. Percentage weight loss of cross-linked oxidized alginate hydrogels as a function of time. Hydrogels were formed at (●) 100 mM and (○) 150 mM adipic dihydrazide and 40 mM CaCl$_2$. All hydrogels were prepared with 10% w/w oxidized alginates (100% equivalents periodate) in dd water.
Figure 21A:
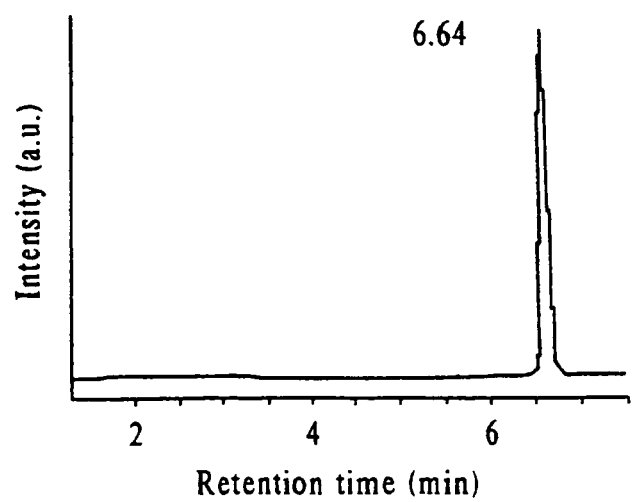
FIG. 21. Reversed phase (Hypersil C18) liquid chromatographic analysis of (a) daunomycin, (b) daunomycin and adipic dihydrazide mixture, and (c) daunomycin released from PAG hydrogels. The mobile phase consisted of H$_2$O/CH$_3$CN (82/18, v/v) and the aqueous component contained 0.025% v/v acetic acid.
Figure 21B:
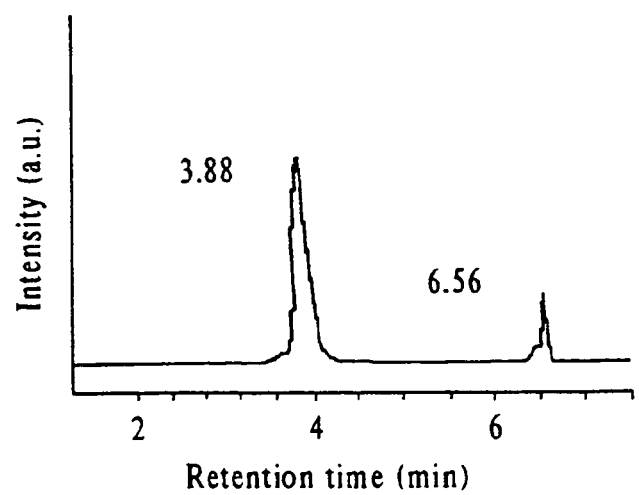
Figure 21C:
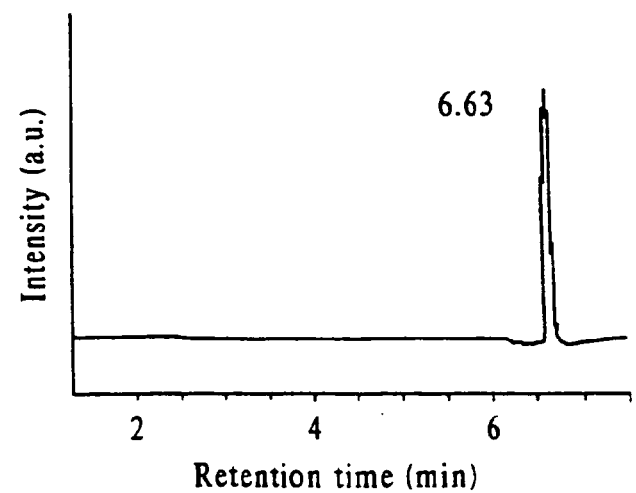
Figure 22:
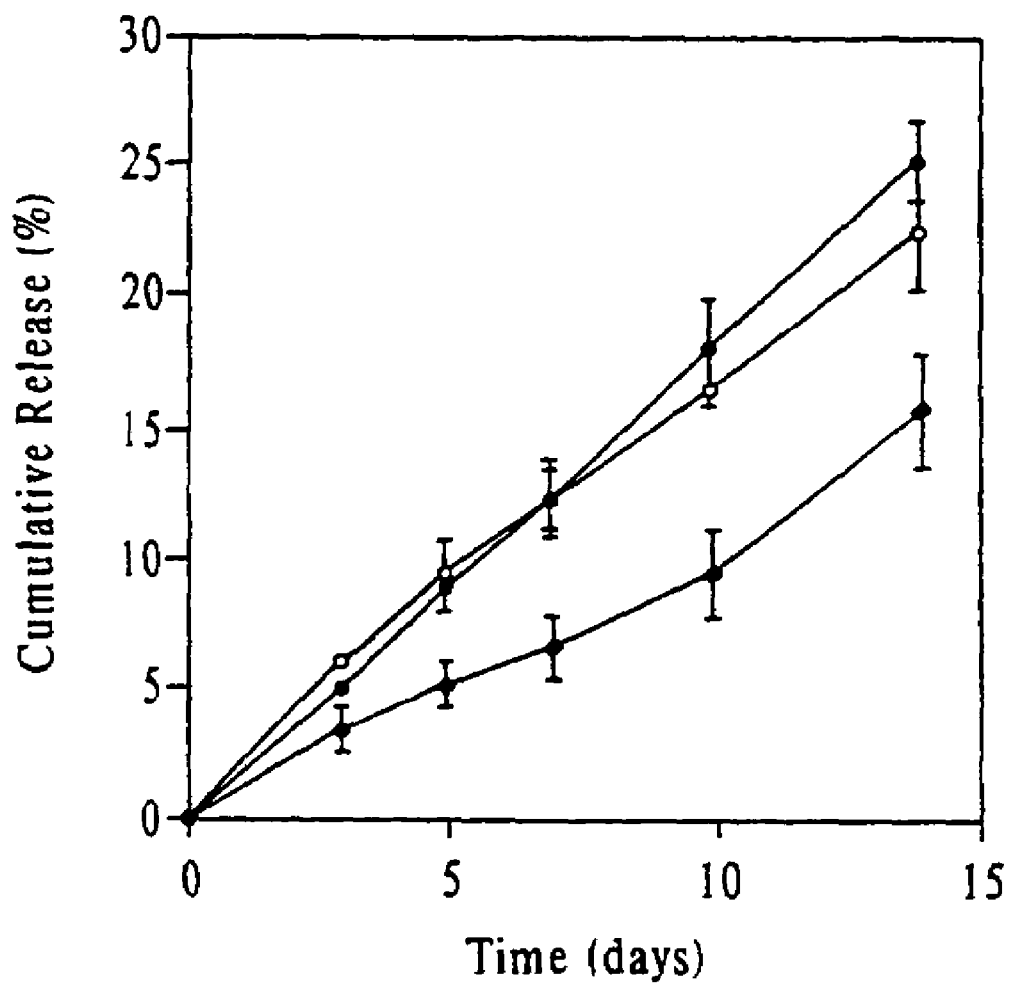
FIG. 22. The cumulative release of daunomycin over time at pH 5 (●), pH 6 (o), and pH 7.4 (♦). All hydrogels were formed with 6% w/w PAG and 150 mM adipic dihydrazide and release was monitored following incubation in DMEM at 37° C.
Figure 23:
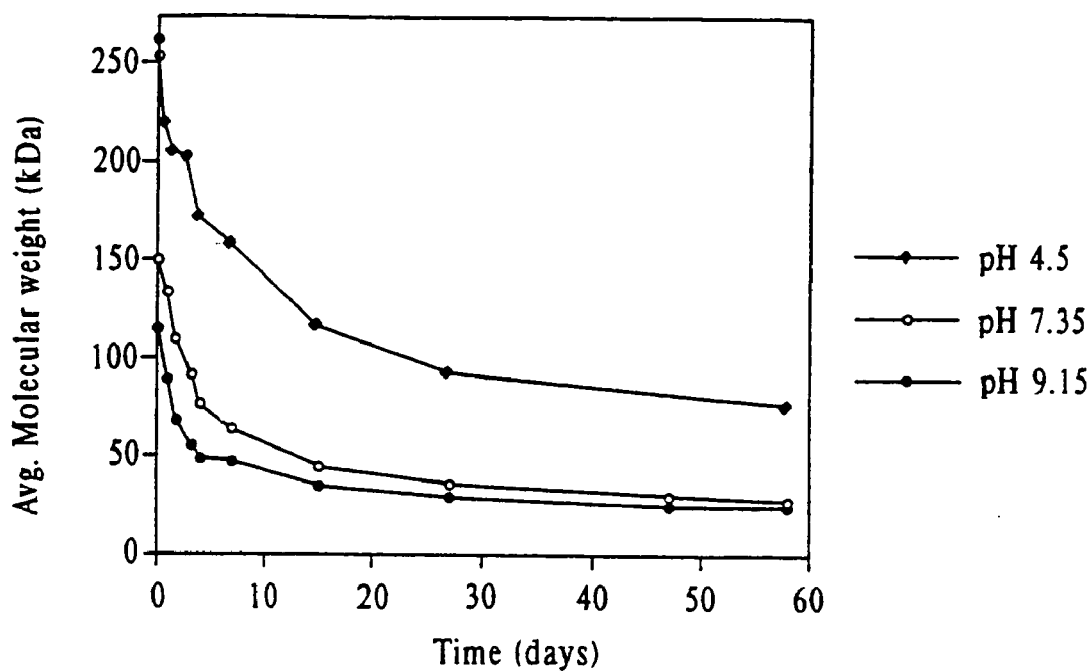
FIG. 23. Graph demonstrating the degradation by hydrolytic cleavage of a high molecular weight alginate oxidized with 5% equivalents of sodium periodate in PBS buffer at physiological 37° C.
Figure 24:
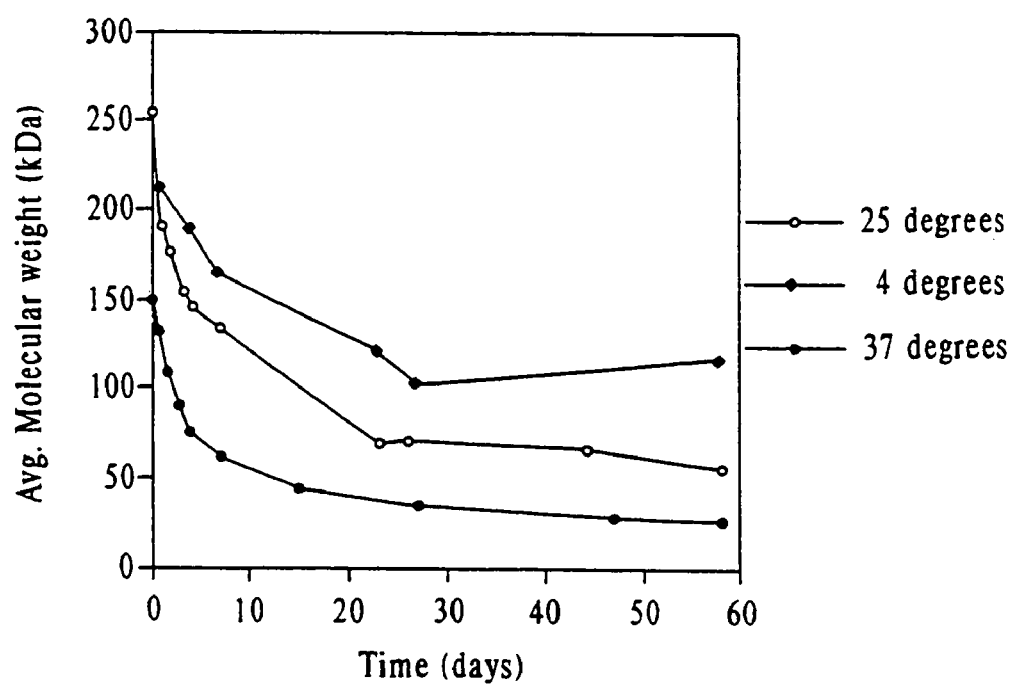
FIG. 24. Graph showing the degradation of high molecular weight oxidized alginate dependent on the temperature of the surrounding medium.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A water-soluble polymer/drug compound which comprises a water-soluble polymer bonded to a drug or prodrug by an in vivo degradeable covalent bond, wherein the bond is provided by a linking compound having two or more hydrazide groups which react with the polymer and drug to form separate hydrazone bonds to each of the polymer and the drug, and wherein the water-soluble polymer is a poly(vinyl alcohol), an alginate modified to convert at least a portion of its guluronate units to aldehyde guluronate units, a polyamine dendrimer, a poly(ethylene glycol) dendrimer, a poly(allyl amine), a poly(vinyl amine), a polyacrylamide or a polyalkyl(meth)acrylate, wherein the linking compound is adipic acid dihydrazide" after "polyalkyl(meth)acrylate.

2. The compound of claim 1, wherein the drug, in its active form, has a ketone or aldehyde group which forms the hydrazone bond.

3. The compound of claim 1, wherein the drug is a chemotherapy drug or the prodrug is a prodrug form of a chemotherapy drug.

4. The compound of claim 1, wherein the drug is a growth factor or the prodrug is a prodrug form of a growth factor.

5. The compound of claim 1, wherein the drug is a steroid or the prodrug is a prodrug form of a steroid.

6. The compound of claim 1, wherein the drug is an anthracycline.

7. The compound of claim 1, wherein the drug is mitoxanthrone or cisplatin.

8. A method for drug delivery which comprises administering to a patient a compound of claim 1.

9. The method of claim 8, wherein the compound is administered by injection.

10. The compound of claim 1, wherein the drug is an taxol or taxotere.

11. The compound of claim 1, wherein the drug is a bleomycin, mitomycin, or plicamycin or a platinum complex with amine groups.

12. The compound of claim 1, wherein the polymer is a poly(vinyl alcohol).

13. The compound of claim 1, wherein the polymer is an alginate modified to convert at least a portion of its guluronate units to aldehyde guluronate units.

* * * * *

UNITED STATES PATENT AND TRADEMARK OFFICE
CERTIFICATE OF CORRECTION

PATENT NO.       : 7,186,413 B2                                         Page 1 of 1
APPLICATION NO.  : 10/445026
DATED            : March 6, 2007
INVENTOR(S)      : Kamal H. Bouhadir It is certified that error appears in the above-identified patent and that said Letters Patent is hereby corrected as shown below:

Column 40, line 5 reads "after "polyalkyl(meth)acrylate" should read -- after polyalkyl(meth)acrylate --

Signed and Sealed this

Seventh Day of August, 2007

JON W. DUDAS
*Director of the United States Patent and Trademark Office*